US012144630B2

(12) United States Patent
Makeyev

(10) Patent No.: US 12,144,630 B2
(45) Date of Patent: Nov. 19, 2024

(54) DETERMINATION OF OPTIMAL LAPLACIAN ESTIMATES AND OPTIMAL INTER-RING DISTANCES FOR CONCENTRIC RING ELECTRODES

(71) Applicant: Diné College, Tsaile, AZ (US)

(72) Inventor: Oleksandr Makeyev, Tsaile, AZ (US)

(73) Assignee: DINÉ COLLEGE, Tsaile, AZ (US)

( * ) Notice: Subject to any disclaimer, the term of this patent is extended or adjusted under 35 U.S.C. 154(b) by 1584 days.

(21) Appl. No.: 16/417,422

(22) Filed: May 20, 2019

(65) Prior Publication Data

US 2020/0367781 A1    Nov. 26, 2020

(51) Int. Cl.
| | |
|---|---|
| *A61B 5/291* | (2021.01) |
| *A61B 5/00* | (2006.01) |
| *A61N 1/04* | (2006.01) |
| *A61N 1/05* | (2006.01) |

(52) U.S. Cl.
CPC ............ *A61B 5/291* (2021.01); *A61B 5/4094* (2013.01); *A61N 1/04* (2013.01); *A61N 1/0531* (2013.01); *A61B 2562/125* (2013.01); *Y10T 29/49002* (2015.01)

(58) Field of Classification Search
None
See application file for complete search history.

(56) References Cited

U.S. PATENT DOCUMENTS

| | | |
|---|---|---|
| 7,043,292 B2 | 5/2006 | Tarjan |
| 8,190,248 B2 | 5/2012 | Besio |
| 8,352,012 B2 | 1/2013 | Besio |
| 8,615,283 B2 | 12/2013 | Besio |

(Continued)

FOREIGN PATENT DOCUMENTS

WO    2013135931 A1    9/2013

OTHER PUBLICATIONS

Makeyev ("Analytic assessment of Laplacian estimates via novel variable interring distances concentric ring electrodes." 2016 38th Annual International Conference of the IEEE Engineering in Medicine and Biology Society (EMBC). IEEE, 2016) (Year: 2016).*

(Continued)

*Primary Examiner* — Roy Y Yi
(74) *Attorney, Agent, or Firm* — Kilpatrick Townsend & Stockton LLP

(57) ABSTRACT

A concentric ring electrode (CRE) is provided that can sense characteristics of an electric potential, such as its Laplacian, more accurately than previous systems. The disclosed system and methods can optimize estimates of the Laplacian based on potentials measured by the CRE's electrodes, and can optimize the geometry of the CRE, in particular the ring electrodes' radii. Given the CRE's geometrical configuration, the system estimates the Laplacian's dependence on the measured potentials by computing a null space of a matrix associated with a series expansion of the potential. The system determines coefficients for the dependence, wherein a first coefficient is between −10 and 10 times, or between −6.5 and −7.5 times, a second coefficient. The system can optimize ranges for the radii by canceling at least one truncation term of the series expansion, estimating a higher-order truncation term as a function of the radii, and minimizing this estimated function.

35 Claims, 14 Drawing Sheets

(56) References Cited

U.S. PATENT DOCUMENTS

| | | | |
|---|---|---|---|
| 8,626,259 | B2 | 1/2014 | Besio |
| 2003/0187490 | A1* | 10/2003 | Gliner ................. A61N 1/0531 607/116 |
| 2006/0173510 | A1 | 8/2006 | Besio |
| 2007/0255085 | A1* | 11/2007 | Kishawi ................. A61N 7/00 600/13 |
| 2011/0137381 | A1* | 6/2011 | Lee ................. A61N 1/36025 607/62 |
| 2012/0310298 | A1 | 12/2012 | Besio |

OTHER PUBLICATIONS

Makeyev, O., "Solving the general inter-ring distances optimization problem for concentric ring electrodes to improve Laplacian estimation," BioMed Eng OnLine (2018) 17:117; https://doi.org/10.1186/s12938-018-0549-6; Aug. 30, 2018; 21 pages.

Makeyev, O., "Optimizing the Design of Noninvasive Concentric Ring Electrodes for Electrophysiological Measurement," Poster Abstract, 5th National Science Foundation Tribal Colleges and Universities Program Research Symposium (TRS18) on May 24, 2018; 1 page.

Makeyev, O., "Optimizing the Design of Noninvasive Concentric Ring Electrodes for Electrophysiological Measurement," Poster, 5th National Science Foundation Tribal Colleges and Universities Program Research Symposium (TRS18) on May 24, 2018; 1 page.

Makeyev, O. et al.; "Improving the accuracy of Laplacian estimation with novel multipolar concentric ring electrodes," Nov. 2015; Measurement 80 (2016) 44-52; 9 pages.

Makeyev, O. et al.; "Proof of concept Laplacian estimate derived for noninvasive tripolar concentric ring electrode with incorporated radius of the central disc and the widths of the concentric rings*," 2017 39th Annual International Conference of the IEEE Engineering in Medicine and Biology Society (EMBC), Jeju Island, South Korea, Jul. 11-15, 2017. IEEE 2017, ISBN 978-1-5090-2809-2; pp. 841-844, 4 pages.

Makeyev, O. et al.; "Improving the Accuracy of Laplacian Estimation with Novel Variable Inter-Ring Distances Concentric Ring Electrodes," Jun. 10, 2016; Sensors 2016, 16, 858; doi:10.3390/s16060858; 16 pages.

* cited by examiner

DETERMINATION OF OPTIMAL LAPLACIAN ESTIMATES AND OPTIMAL INTER-RING DISTANCES FOR CONCENTRIC RING ELECTRODES

STATEMENT AS TO RIGHTS TO INVENTIONS MADE UNDER FEDERALLY SPONSORED RESEARCH AND DEVELOPMENT

This invention was made with government support under award number 1622481 to Oleksandr Makeyev, awarded by the National Science Foundation (NSF) Division of Human Resource Development (HRD) Tribal Colleges and Universities Program (TCUP). The government has certain rights in the invention.

BACKGROUND OF THE INVENTION

Electroencephalography (EEG) is an essential tool for brain and behavioral research, as well as one of the mainstays of hospital diagnostic procedures and pre-surgical planning. Despite EEG's many advantages, the technology faces challenges such as poor spatial resolution, selectivity and low signal-to-noise ratio.

Noninvasive concentric ring electrodes (CREs) can resolve many of these problems. Noninvasive CREs have been shown to estimate the surface Laplacian, the second spatial derivative of the potentials on the scalp surface for the case of electroencephalogram (EEG), directly at each electrode instead of combining the data from an array of conventional, single pole, disc electrodes. Compared to EEG via disc electrodes, EEG via tripolar CREs (tEEG) has been demonstrated to have significantly better spatial selectivity, signal-to-noise ratio, and mutual information. CREs have found applications in a wide range of areas including brain-computer interfaces, epileptic seizure onset detection, detection of high-frequency oscillations, which may typically predict or precede seizures, and seizure onset zones, as well as in applications involving electroenterograms, electrocardiograms (ECG), and electrohysterograms. CREs could also be used for electrophysiological monitoring, e.g., during surgery.

However, the effect of CRE geometry on performance has remained relatively poorly investigated. Conventional CRE systems have not made full use of variations to the CRE's geometrical configuration, such as the radii, spacing, and width of the ring electrodes, in order to improve performance. Moreover, existing estimates for the Laplacian from CRE measurements do not make optimal use of the information measured by the CRE.

BRIEF SUMMARY OF THE INVENTION

Disclosed is a system and methods for determining values for a set of radii of a plurality of rings of a concentric ring electrode (CRE), the plurality of rings including an inner ring and an outer ring. The system may receive information specifying a quantity of rings in the plurality of rings and a total radius of the CRE. The system may then estimate, based on canceling at least a first truncation term of a series expansion of an electrostatic potential, a dependence of a functional of the electrostatic potential on (i) the total radius, (ii) the set of radii, and (iii) a set of potential differences, wherein a respective radius and a respective potential difference correspond to a respective ring of the plurality of rings. The system may then determine a remaining truncation term of the series expansion as a function of the total radius and the set of radii, the remaining truncation term having a lowest order higher than twice the quantity of rings. The system may then minimize in absolute value the remaining truncation term as the function of the set of radii to determine optimum values for the set of radii in terms of the total radius.

In another aspect of this disclosure, the system and methods can determine a functional of an electrostatic potential, the electrostatic potential measurable by a concentric ring electrode (CRE) comprising at least an inner ring and an outer ring. The system may receive information specifying a geometrical configuration of the CRE. The system may then estimate a dependence of the functional on a set of potential differences comprising at least a first potential difference corresponding to the inner ring and a second potential difference corresponding to the outer ring, by at least determining a null space of a matrix associated with a series expansion of the electrostatic potential for the geometrical configuration. Estimating the dependence of the functional on a set of potential differences may further include determining, based on the null space, a set of coefficients for the dependence, the set of coefficients comprising at least a nonzero first coefficient of the first potential difference and a nonzero second coefficient of the second potential difference, wherein the first coefficient is between −10 and 10 times the second coefficient.

DETAILED DESCRIPTION OF THE INVENTION

Figure 1A:
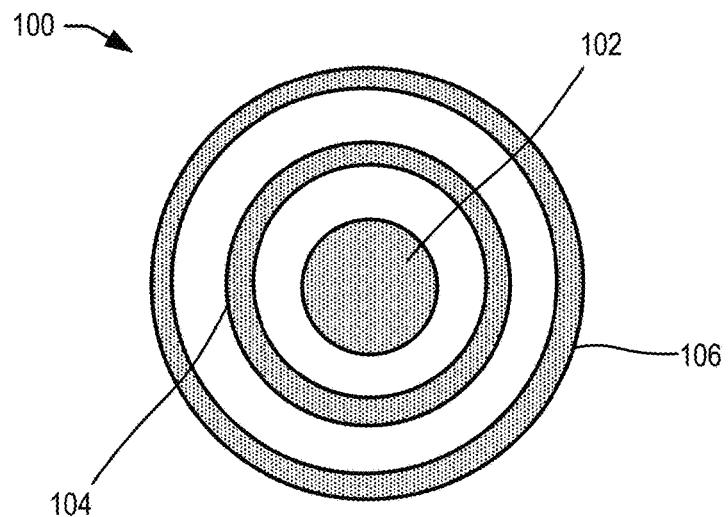
FIG. 1A illustrates an example structure of a tripolar concentric ring electrode (CRE), in accordance with an embodiment.

Noninvasive concentric ring electrodes (CREs) can improve significantly on the performance of electroencephalography (EEG) systems. Noninvasive CREs can estimate the surface Laplacian, the second spatial derivative of the potentials on the scalp surface for EEG, directly at each electrode instead of combining the data from an array of conventional, single pole, disc electrodes. In particular, the disclosed system and methods can determine a formula or linear combination coefficients relating the potentials measured by a CRE to the Laplacian. The CRE can further be designed to use a custom amplifier or preamplifier board, or other hardware, to determine the Laplacian based on such a formula or coefficients, thereby reducing the computational burden compared to conventional electrodes. However, note that the CREs may also be arranged in arrays in order to monitor and/or map the Laplacian at different locations. Compared to EEG via disc electrodes, EEG via tripolar CREs (tEEG) has significantly better spatial selectivity, signal-to-noise ratio, and mutual information. CREs have found applications in a wide range of areas including brain-computer interface, epileptic seizure onset detection, detection of high-frequency oscillations and seizure onset zones, as well as in applications involving electroenterograms, electrocardiograms (ECG), and electrohysterograms. CREs could also be used for electrophysiological monitoring, e.g. during surgery.

However, the effect of CRE geometry on performance has remained relatively poorly investigated. CRE systems have not made full use of variations in the CRE's geometrical configuration, such as the radii, spacing, and width of the ring electrodes. Moreover, existing estimates for the Laplacian from CRE measurements do not make optimal use of the information measured by the CRE.

The disclosed system and methods can improve over conventional systems by providing an optimized geometry for CREs with any number of rings and optimized formulas and/or coefficients to estimate the surface Laplacian of the potential based on measurements by the CRE's recording sites. In particular, the system can optimize the accuracy of measurement of the surface Laplacian by linearly combining the measurements of the CRE's (n+1) recording sites, so as to cancel as many truncation terms as possible in a series expansion of the Laplacian. The system can further take advantage of freedom to adjust the CRE's geometry, such as the radii of the CRE's rings, and thereby further reduce the measurement error of the surface Laplacian. The system can optimize the linear combination coefficients and/or the ring radii for CREs with any number n of rings, and with arbitrary radial configuration of the rings. Further, the system can account for finite ring thickness and central disc area.

Accordingly, the disclosed systems can improve over conventional systems and devices that measure electrostatic potentials by measuring these potentials more accurately, due both to the improved geometrical arrangement of the CRE rings, and to the optimized estimation for any given geometry. Such improvements can lead to improved patient experiences such as shorter and/or less invasive procedures, as well as to improved health outcomes such as improved diagnostic and preventive measures. Moreover, the disclosed systems, devices, and methods may provide cost savings and efficiency improvements, for example, by enabling more accurate readings with fewer recording sites and/or fewer electrodes. In particular, the optimized linear combination coefficients may provide cost improvements by obviating the need to upgrade or replace existing CRE equipment.

FIG. 1A illustrates an example structure of a tripolar concentric ring electrode (CRE) 100, in accordance with an embodiment. The CRE 100 may include multiple recording surfaces, such as a central disc 102, an inner ring 104, and an outer ring 106. In an embodiment, these recording surfaces may be composed of one or more metals or conductive materials, including but not limited to silver, gold, copper, tin, aluminum, silver chloride, or any other conductor. In some embodiments, the recording surfaces may also contain other materials, such as non-conducting materials. The recording surfaces may be separated by dielectrics, such as empty space or air, or any other dielectric or insulating material. In some embodiments, the CRE 100 may be mounted on, or contact, a patient's head or scalp, in order to perform electroencephalography (EEG). In particular, the CRE 100 may measure the surface Laplacian, or the second spatial derivative, of the electrostatic potential on the patient's scalp surface. In various embodiments, CRE 100 may be used for brain-computer interfaces, epileptic seizure onset detection, detection of high-frequency oscillations, which may typically predict or precede seizures, and seizure onset zones, as well as in applications involving electroenterograms, electrocardiograms (ECG), electrohysterograms, or any other kind of electrophysiological monitoring, e.g. during surgery.

In an embodiment, the CRE 100 may be used to measure the electric potential at the recording surfaces, or an average of the potential over the areas of the respective recording surfaces. In an embodiment, the measured ring potentials may be relative to a reference potential such as the central disc's potential, for example the respective potentials associated with rings 104 and 106 may be measured and/or expressed as differences from the potential of the central disc 102. In turn, these potential measurements may be used to estimate a surface Laplacian, or second spatial derivative $$\Delta v_0 \equiv \left( \frac{\partial^2}{\partial x^2} + \frac{\partial}{\partial y^2} \right) v_0,$$

of the electric potential $v_0$, near the center of CRE 100 or central disc 102, according to the system and techniques described herein. The potentials or potential differences may also be referred to herein as voltages. Note that the spatial coordinates x and y represent coordinates in the plane of the CRE. For example, if the CRE is configured parallel to a patient's scalp in order to measure the surface Laplacian along the scalp, the xy-plane may be parallel to the scalp.

In a typical example, the number of rings, also referred to as n, is a key parameter governing the CRE. Because the CRE may have a central disc recording surface 102, in addition to the ring recording surfaces, a CRE with n rings is also referred to as a (n+1)-polar CRE. In this example, the tripolar CRE 100 has two concentric rings, an inner ring 104 and an outer ring 106. In a typical example, central disc 102 may have a radius r, while inner ring 104 may have a radius 2r and outer ring 106 may have a radius 3r. Other geometries are possible, and are not limited by the present disclosure. In some examples, the radii of the concentric rings may be expressed in terms of the radius of the outer ring. For example, the disclosed system and method may treat the radius of the outermost ring as a parameter and/or receive the outermost ring radius as an input, and may output optimized values of the other ring radii as fractions of the outermost ring radius.

Figure 1B:
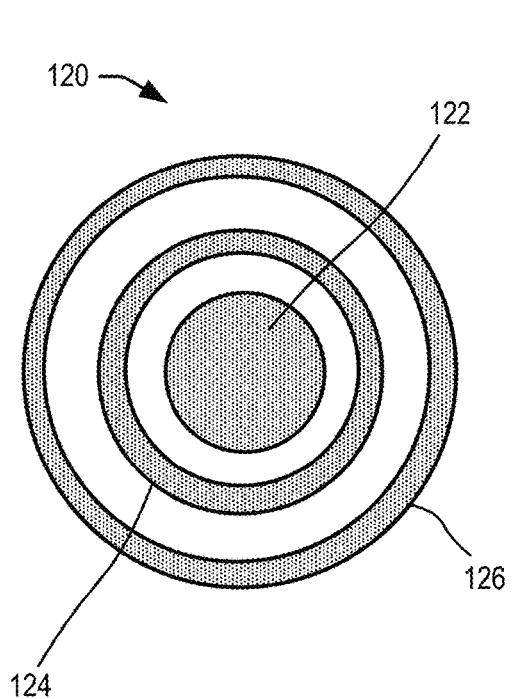
FIG. 1B illustrates an alternative example structure of a tripolar CRE.

FIG. 1B illustrates an alternative example structure of a tripolar CRE 120. In this example, the central disc 122 is larger than central disc 102 of the example of FIG. 1A, but the rings 124 and 126 remain the same size as rings 104 and 106 of FIG. 1A. As a result, the ratios of various geometrical features of CRE 120 differ from those of CRE 100 in FIG. 1A. For example, the central disc radius as a fraction of outer ring radius is greater for CRE 120 than for CRE 100. Similarly, in this example, the inter-ring separations may be considered to vary for CRE 120 because the radial separation from ring 124 to the outer surface of central disc 122 may be less than the radial separation from ring 126 to ring 124. By contrast, CRE 100 in the example of FIG. 1A may have constant inter-ring separations. The inter-ring separations may also be referred to herein as inter-ring distances or intervals.

In some embodiments, the disclosed system and methods may make use of such geometrical or other variations in order to improve performance. For example, varying the ring radii or inter-ring separations may improve the measurement performance, sensitivity, and/or accuracy of the CRE. As mentioned above, the system can also improve the accuracy of measurement of the surface Laplacian by optimizing coefficients so as to cancel as many truncation terms as possible. Such improvements can lead to improved patient experiences such as shorter procedures, as well as to improved health outcomes. Moreover, the disclosed system may provide cost savings, for example, by enabling accurate readings with less equipment, or by obviating the need to upgrade or replace existing CRE equipment.

Other variations are also possible, such as: geometrical variations (e.g., using non-concentric or non-circular rings, or otherwise varying the sizes, separations, number, or shapes of recording surfaces); material or composition variations (e.g., using different metals or alloys for the recording surfaces, varying the materials of different recording surfaces within a single CRE, etc.); or other variations, and are not limited by the present disclosure. Furthermore, the system may also optimize coefficients to estimate a potential Laplacian, and/or optimize other aspects of methods for estimating the Laplacian, or other electrical characteristics measured by the CRE, as described herein below.

Figure 1C:
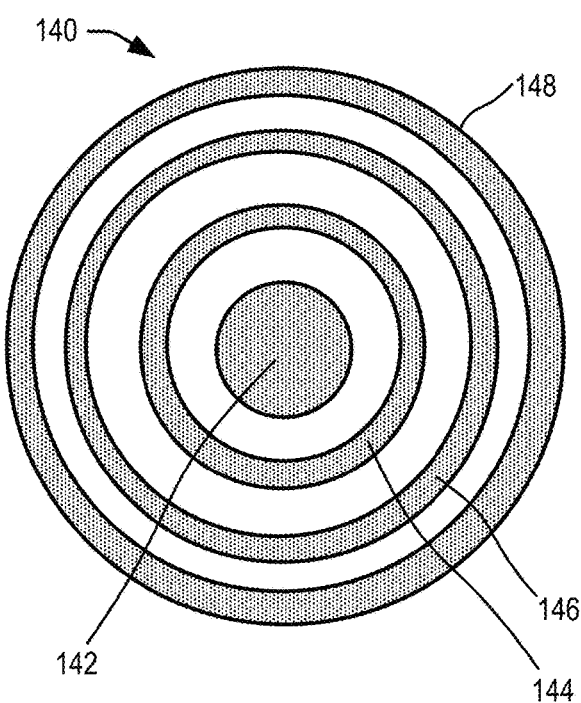
FIG. 1C illustrates an example structure of a quadripolar CRE.

FIG. 1C illustrates an example structure of a quadripolar CRE 140 with three rings. In this example, the central disc 142 and two inner rings 144 and 146 of CRE 140 have similar sizes, shapes, and separations compared with the central disc 102 and rings 104 and 106 of CRE 100 in the example of FIG. 1A. However, CRE 140 also includes an additional ring 148, for a total of three rings, or four recording surfaces including the central disc 142.

In some examples, CREs with additional recording surfaces, such as additional ring 148, may have improved measurement performance, sensitivity, and/or accuracy. In an example, an estimate of the surface Laplacian of the electrostatic potential near the central disc 142 or the center of the CRE may improve systematically as the number of rings is increased. In some embodiments, the CRE can have any number of rings, and is not limited by the present disclosure. However, in order to make optimal use of the additional recording surfaces, the system may combine the measured potentials based on a formula and/or coefficients that are optimized for the particular geometry of the CRE, as disclosed herein. Thus, in general, the formula and/or set of coefficients may depend on the number n of rings.

For example, the system may make use of a different set of coefficients for a CRE with n rings than it does for a CRE with a different number m of rings. For example, coefficients associated with the inner rings 144 and 146 of quadripolar CRE 140 may differ from the respective coefficients associated with rings 104 and 106 of the tripolar CRE 100 of FIG. 1A. Of course, the system can also use a coefficient associated with outermost ring 148 of quadripolar CRE 140, which has no counterpart ring in tripolar CRE 100. Moreover, in some embodiments, such a coefficient associated with outermost ring 148 may also differ from the coefficient associated with ring 106 of the tripolar CRE 100, even though ring 106 is the outermost ring of CRE 100.

Figure 2A:
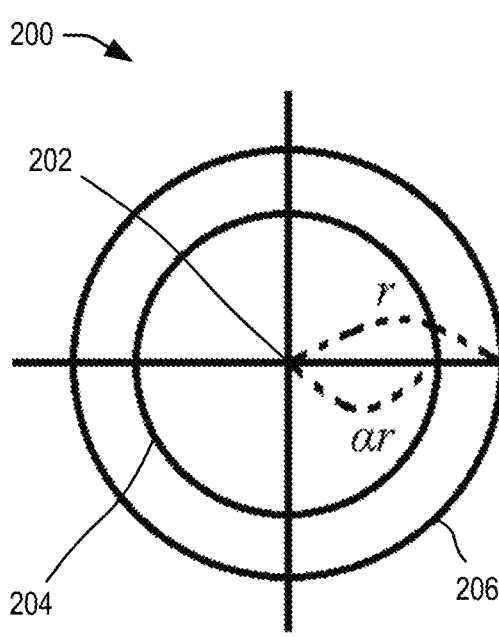
FIG. 2A illustrates a diagrammatic view of an example tripolar concentric ring electrode (CRE), in accordance with an embodiment.

FIG. 2A illustrates a diagrammatic view of an example tripolar CRE 200, in accordance with an embodiment. In this example, tripolar CRE 200 includes a central disc 202 (modeled in this example as a point) and rings 204 and 206. In some cases, the radii of the concentric rings may be expressed in terms of the radius of the outer ring. For example, the radius of outermost ring 206 may have a value r, and the radius of inner ring 204 may have a value $\alpha r$, where $\alpha$ is a dimensionless ratio. Accordingly, the system may optimize the ratio $\alpha$ and/or may express the radius of inner ring 204 as the ratio $\alpha$. For example, the disclosed system and method may treat the radius r of the outermost ring 206 as a parameter and/or receive the outermost ring radius r as an input, and may output optimized values of the other ring radii, such as the radius $\alpha r$ of inner ring 204, as a fraction $\alpha$ of the outermost ring radius.

Figure 2B:
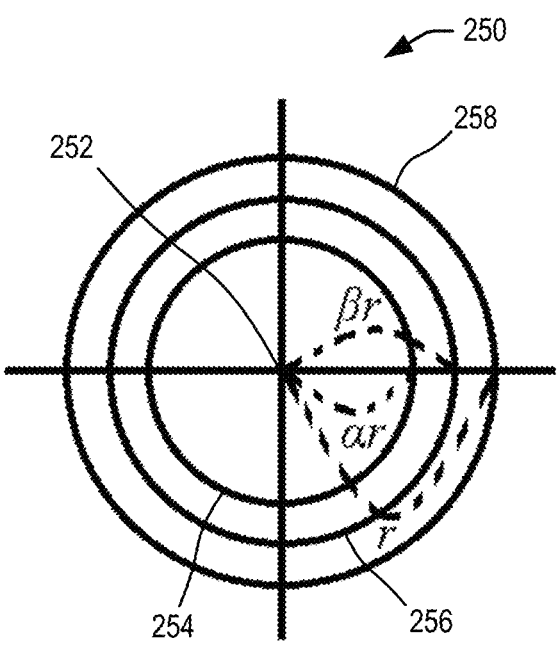
FIG. 2B illustrates a diagrammatic view of an example quadripolar concentric ring electrode, in accordance with an embodiment.

FIG. 2B illustrates a diagrammatic view of an example quadripolar CRE 250, in accordance with an embodiment. In this example, quadripolar CRE 250 includes central disc 252 (modeled in this example as a point) and rings 254, 256, and 258. In this example, the radius of outermost ring 258 may have a value r, while the radius of innermost ring 254 may have a value $\alpha r$, and the radius of middle ring 256 may have a value $\beta r$, where $\alpha$ and $\beta$ are dimensionless ratios. Accordingly, the system may optimize the ratios $\alpha$ and $\beta$, and/or may express the radii of rings 254 and 256 as the ratios $\alpha$ and $\beta$. For example, the disclosed system and method may treat the radius r of the outermost ring 258 as a parameter and/or receive r as an input, and may output optimized values of the other ring radii as fractions $\alpha$ and $\beta$ of r.

In some embodiments, the system can treat the ratios $\alpha$ and $\beta$ of the examples of FIGS. 2A and 2B as variables to be optimized, as described herein and in "Solving the General Inter-Ring Distances Optimization Problem for Concentric Ring Electrodes to Improve Laplacian Estimation" by O. Makeyev, BioMed Eng OnLine (2018), hereby incorporated by reference. Some related techniques are also described in: "Improving the accuracy of Laplacian estimation with novel multipolar concentric ring electrodes" by O. Makeyev, Q. Ding, and W. G. Besio, Measurement (2016); "Improving the Accuracy of Laplacian Estimation with Novel Variable Inter-Ring Distances Concentric Ring Electrodes" by O. Makeyev and W. G. Besio, Sensors (2016); and "Proof of concept Laplacian estimate derived for non-invasive tripolar concentric ring electrode with incorporated radius of the central disc and the widths of the concentric rings" by O. Makeyev, IEEE EMBC (2017), the disclosures of which are hereby incorporated by reference.

As described herein, the system can optimize the geometry of a CRE with any number n of rings, such as by determining optimal ring radii and/or other geometrical features of the CRE. The disclosed system can further optimize formulas and/or coefficients in order to accurately estimate the surface Laplacian of the electric potential based on the CRE's measurements.

I. Estimating Laplacian Via Negligible Dimensions Model (NDM)

The system can estimate the Laplacian $$\Delta v_0 \equiv \left( \frac{\partial^2}{\partial x^2} + \frac{\partial^2}{\partial y^2} \right) v_0$$

(also denoted as $\nabla^2 v_0$) of the electrostatic potential $v_0$ near the center of a (n+1)-polar CRE with n rings and constant inter-ring separations. In an embodiment, the system may apply a negligible dimensions model (NDM), such as a (4n+1)-point method, to estimate the Laplacian. The NDM may treat the central disc and concentric rings of the CRE by approximating them as a point at the center of the CRE, and as circles concentric about the center of the CRE, respectively. In particular, the (4n+1)-point method may average the potential over four points on each concentric ring of the CRE. For example, a five-point method (FPM) may apply to a case of a CRE with only one ring, a nine-point method (NPM) to a tripolar CRE with two rings, a thirteen-point method to a quadripolar CRE with three rings, etc. Alternatively, other numbers of points may be averaged over a respective ring. The spatial coordinates x and y may represent coordinates in the plane of the CRE, for example, parallel to a surface such as a patient's scalp being measured via the CRE.

A. Equal Inter-Ring Separations

Figure 3A:
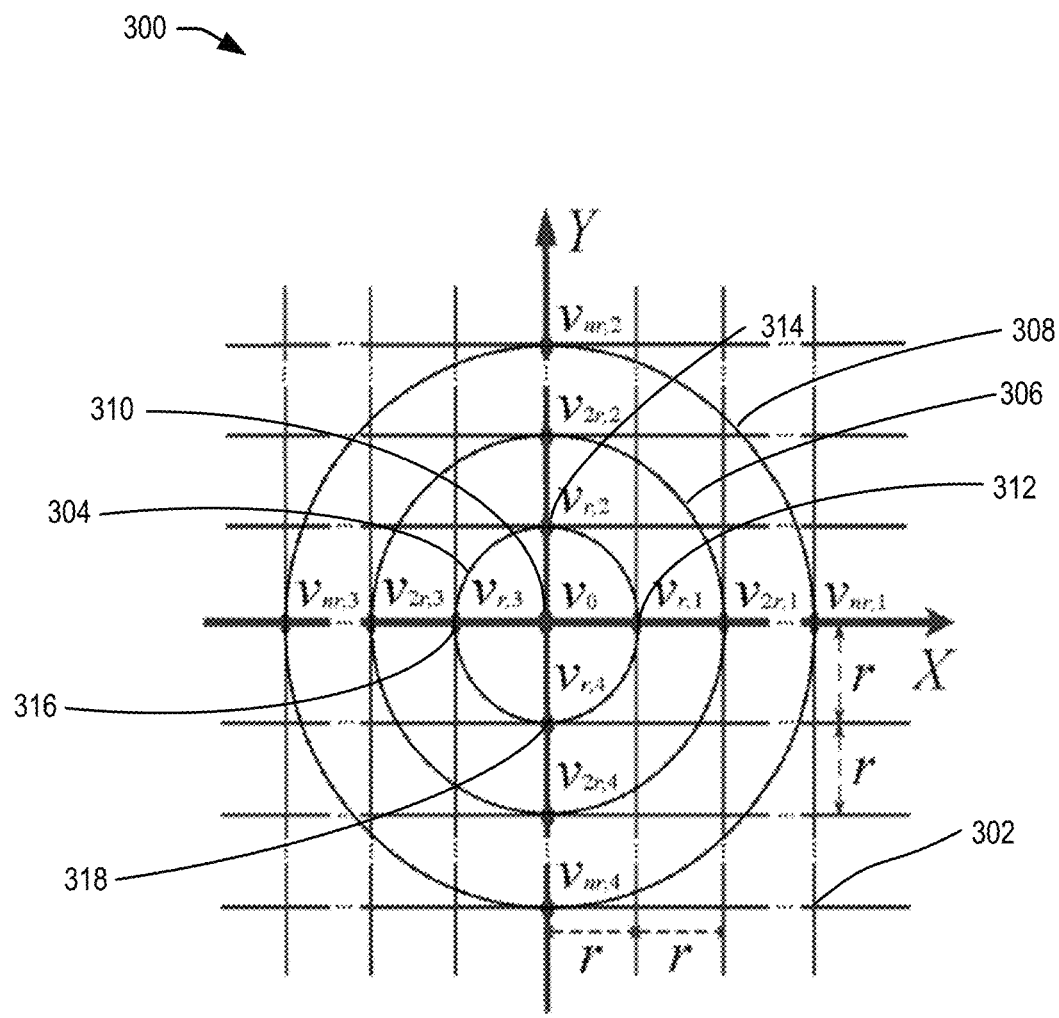
FIG. 3A illustrates an example geometry of a CRE used in series expanding an electric potential to estimate the potential's Laplacian, according to embodiments.

FIG. 3A illustrates an example geometry of a CRE 300 used in series expanding an electric potential to estimate the potential's Laplacian, according to embodiments. In the example of FIG. 3A, the NDM may be illustrated by means of a regular square grid 302, with all inter-point distances equal to r. In this example, the CRE 300 is an (n+1)-polar CRE, with a central disc represented by central point 310, and n concentric rings, including first or innermost ring 304 with radius r, second ring 306 with radius 2r, and nth ring 308 with radius nr. In various embodiments, the system can estimate the potential's Laplacian for a CRE 300 with any number n of rings.

In a typical example, the potential of a respective ring of CRE 300 may be regarded as the potential difference between the respective ring and the central disc, wherein the potential of the central disc may be regarded as a reference potential. Note that the potentials of the respective recording sites (i.e., the respective concentric rings and the central disc) may be measured and recorded independently, before these respective potential differences are computed. In various embodiments, the differences can be computed via software, hardware, and/or analog methods such as a custom amplifier or preamplifier, and are not limited by the present disclosure.

In some embodiments, the potential of a respective recording site, such as a respective ring or the central disc, may be averaged over some or all of the respective site, or the site's surface. This averaging may proceed as disclosed herein, for example, but not limited to, by a five-point method (FPM), a nine-point method (NPM), a thirteen-point method, etc. In some examples, the recording sites may be conductors, such that the potential is substantially constant on a respective site. Note that terms such as "the potential difference associated with a ring" may be used herein to refer to the potential of a ring minus the potential of the central disc. However, other measures of the potential of particular rings may also be possible, including but not limited to the potential of each ring relative to some other reference potential, such as a ground, and such usages are not limited by the present disclosure.

In this example, an NDM, such as the nine-point method (NPM), can be applied to calculate and/or average the potentials on the rings from points on the rings, such as points distributed around circles representing or modeling the rings 304, 306, and 308. In various embodiments, the system may use any number of points to calculate and/or average the potentials on the recording sites, and is not limited by the present disclosure.

Note that, in some embodiments, the CRE 300 may possess, or approximately possess, cylindrical symmetry, that is, two-dimensional rotational symmetry about the CRE's center 310. However, the potential being measured by CRE 300 may not necessarily possess such symmetry, in particular because the CRE may measure electrical activity originating from a target without such symmetry, for example a human brain or heart. Accordingly, the point potentials averaged by the FPM or other method, such as at points 312, 314, 316, and 318 distributed around circle 304, may or may not be equal before averaging. However, averaging and/or applying an FPM, NPM, etc., may enable the system to analyze the potential and/or Laplacian without needing to explicitly consider such variations around the circle. Moreover, note that, in some embodiments, the potential on or inside a respective recording site of the CRE 300 may be substantially constant, by virtue of the recording sites 304, 306, 308, and 310 containing conductive materials with free charges that can rearrange to minimize any potential differences. In such a case, averaging over a respective recording site, or the area thereof, may provide an approximation of the constant potential value over the surface of the respective recording site.

First, consider an example wherein the FPM is used to approximate the Laplacian of a bipolar CRE with only the single ring 304. In this example, the system may apply the FPM by averaging over points 310, 312, 314, 316, and 318, having potentials $v_0$, $v_{r,1}$, $v_{r,2}$, $v_{r,3}$, and $v_{r,4}$, respectively. In particular, the disclosed system and/or methods may Taylor expand to obtain an average of $v_{r,1}$, $v_{r,2}$, $v_{r,3}$, and $v_{r,4}$ in terms of the potential $v_0$ at central point 310, the Laplacian $\Delta v_0$ of the potential, and higher-order spatial derivatives of the potential v. Note that, in this example, any odd-order terms (such as terms in the first spatial derivative or gradient of the potential v, terms in the third spatial derivative of the potential, etc.) may cancel due to the averaging over points 312, 314, 316, and 318, which are arranged symmetrically about the central point 310. The system and/or methods may further rearrange to solve for the Laplacian in terms of potentials $v_0$, $v_{r,1}$, $v_{r,2}$, $v_{r,3}$, and $v_{r,4}$, and the higher-order derivative terms:

$$\Delta v_0 = \frac{d^2 v}{dx^2} + \frac{d^2 v}{dy^2} = \frac{1}{r^2}\left(\sum_{i=1}^{4} v_{r,i} - 4v_0\right) + O(r^2) \quad (1)$$

$$\text{where } O(r^2) = \frac{r^2}{4!}\left(\frac{d^4 v}{dx^4} + \frac{d^4 v}{dy^4}\right) + \frac{r^4}{6!}\left(\frac{d^6 v}{dx^6} + \frac{d^6 v}{dy^6}\right) + \ldots$$

is the truncation error, which includes higher-order spatial derivatives of the potential v. Note that truncation error may refer herein to a neglected or truncated term in a series expansion such as a Taylor expansion, to a Taylor series remainder or error term, or to another estimate of error. In some embodiments, the system may use another series expansion, such as a Maclaurin expansion, a Laurent expansion, a Fourier expansion, or any other expansion, and is not limited by the present disclosure. The order of the truncation terms may refer herein to a power of r, and/or an order of spatial derivatives, associated with the truncation terms.

Moreover, note that each of points 312, 314, 316, and 318 may be represented in terms of a difference $v_{r,1}-v_0$ between the respective point's potential $v_{r,1}$, $v_{r,2}$, $v_{r,3}$, or $v_{r,4}$, and the potential $v_0$ at central point 310. Thus, equation (1) includes a term $-4 v_0$ in the parentheses, where the factor of 4 results from taking these four differences, i.e. $\Sigma_{i=1}^{4}[v_{r,i}-v_0]=\Sigma_{i=1}^{4}(v_{r,i})-4v_0$.

In an embodiment, the system can generalize this equation (1) by taking an integral along the circle of radius r around the point with potential $v_0$. Note that the system may numerically approximate the integral by using any number of points, and/or weighting the values at different points (e.g., by using Gaussian quadrature weights, numerical integration methods, etc.), and is not limited by the present disclosure. Defining $x=r \cos(\theta)$ and $y=r \sin(\theta)$ results in:

$$\frac{1}{2\pi}\int_{0}^{2\pi} v(r, \theta)d\theta - v_0 = \quad (2)$$

$$\frac{r^2}{4}\Delta v_0 + \frac{r^4}{4!}\int_{0}^{2\pi}\sum_{j=0}^{4}\sin^{4-j}(\theta)\cos^{j}(\theta)d\theta\left(\frac{d^4 v}{dx^{4-j}dy^j}\right) + \ldots$$

$$\text{where } \frac{1}{2\pi}\int_{0}^{2\pi} v(r, \theta)d\theta$$

is the average potential on the ring of radius r and $v_0$ is the potential on the central disc of the CRE.

Next, consider the case of a multipolar CRE 300 with n rings (n≥2), as in FIG. 3A, approximated according to a (4n+1)-point method. In this example, the disclosed system and/or methods may initially construct a set of n FPM equations. In an embodiment, each equation corresponds to one of the n rings. In some embodiments, the ring radii can range from r to nr, for example rings 304, 306, and 308 in FIG. 3A have radii of r, 2r, and nr, respectively (note that CRE 300 may have additional rings not shown between ring 306 and ring 308, with radii from 3r to (n−1)r). Alternatively, the system can also estimate the Laplacian for rings with other radii, as described below.

These n FPM equations may be obtained in a manner similar to how the FPM equation was constructed above for a bipolar CRE with a single ring 304 of radius r. For example, the FPM equation for the ring 308 of radius nr (points with potentials $v_0$, $v_{nr,1}$, $v_{nr,2}$, $v_{nr,3}$, and $v_{nr,4}$ in the example of FIG. 3A) may be given by:

$$\frac{1}{2\pi}\int_{0}^{2\pi} v(nr, \theta)d\theta - v_0 = \quad (3)$$

$$\frac{(nr)^2}{4}\Delta v_0 + \frac{(nr)^4}{4!}\int_{0}^{2\pi}\sum_{j=0}^{4}\sin^{4-j}(\theta)\cos^{j}(\theta)d\theta\left(\frac{d^4 v}{dx^{4-j}dy^j}\right) +$$

$$\frac{(nr)^6}{6!}\int_{0}^{2\pi}\sum_{j=0}^{6}\sin^{6-j}(\theta)\cos^{j}(\theta)d\theta\left(\frac{d^6 v}{dx^{6-j}dy^j}\right) + \ldots$$

$$\text{where } \frac{1}{2\pi}\int_{0}^{2\pi} v(nr, \theta)d\theta$$

is the average potential on the ring 308 of radius nr, and $v_0$ is the potential on the central disc (i.e. at point 310) of the CRE 300.

Finally, to estimate the Laplacian, the n equations, representing differences between average potentials on the n rings and the potential $v_0$ on the central disc of the CRE, can be linearly combined in order to cancel the Taylor series truncation terms up to the order of 2n. To obtain such a linear combination, the coefficients $l^k$ of the truncation terms with the general form $$\frac{(lr)^k}{k!}\int_{0}^{2\pi}\sum_{j=0}^{k}\sin^{k-j}(\theta)\cos^{j}(\theta)d\theta\left(\frac{d^k v}{dx^{k-j}dy^j}\right)$$

for even order k ranging from 4 to 2n and ring radius multiplier l can be arranged into an (n−1) by n matrix A. In a typical example, l may be a purely numerical factor, with a value ranging from 1, as in equation (2), to n, as in equation (3). In particular, ring radius multiplier l may be equal to the radius of the lth ring in units of r. In the example of FIG. 3A, the inter-ring separations are constant, and the lth ring has radius lr, so the ring radius multiplier is simply an integer l that enumerates the corresponding ring. Accordingly, in an embodiment, the (k, l)th element of A is given by $A_{kl}=l^{2(k+1)}$, and the matrix A is a function only of the number of the rings n:

$$A = \begin{pmatrix} 1^4 & 2^4 & \cdots & n^4 \\ 1^6 & 2^6 & \cdots & n^6 \\ \vdots & \vdots & \ddots & \vdots \\ 1^{2n} & 2^{2n} & \cdots & n^{2n} \end{pmatrix} = \begin{pmatrix} 1 & 2^4 & \cdots & n^4 \\ 1 & 2^6 & \cdots & n^6 \\ \vdots & \vdots & \ddots & \vdots \\ 1 & 2^n & \cdots & n^{2n} \end{pmatrix} \quad (4)$$

The null space (or kernel) of matrix A is an n-dimensional vector $\bar{x}=(x_1, x_2, \ldots, x_n)$ that is a nontrivial solution of a matrix equation $A\bar{x}=\bar{0}$. The dot product of $\bar{x}$ and a vector consisting of n coefficients $l^k$ corresponding to all the ring radii [i.e. $(1, 2^k, \ldots, n^k)$] for all even orders k ranging from 4 to 2n is equal to 0:

$$x_1 + 2^k x_2 + \ldots + n^k x_n = 0 \qquad (5)$$

In some embodiments, by solving for the null space vector $\bar{x}$ of the matrix A, the system determines coefficients for the linear combination of the averaged potential differences so as to cancel an optimal number of truncation terms and obtain an estimate of the potential's Laplacian. Note that the system may subsequently substitute the values of the potentials or potential differences measured by the CRE's respective recording sites for these averaged potential differences in order to determine an estimate of the Laplacian based on these CRE measurements. In general, the greater the number of truncation terms canceled, the more precise the resulting Laplacian estimate is likely to be. Because the NDM may provide n equations for the n rings, it is possible to form linear combinations of these equations that cancel even-order truncation terms from a lowest order of 4 up to a highest order m, which can depend on n. Here the order of the canceled truncation terms refers to the power of r, as well as the order of spatial derivatives, in the canceled truncation terms. Note that the odd-order truncation terms may cancel due to averaging about circles, as described above.

Thus the number of rows in A may equal the number of canceled truncation terms from 4 to m, given by $(m-2)/2$. However, note that it may be necessary for matrix A to be underdetermined in order for a non-trivial null space vector $\bar{x}$ to exist. As a result, in some embodiments, A may be required to have fewer rows than columns. Accordingly, with n equations for the n rings, in order for a non-trivial null space vector $\bar{x}$ to exist, m must satisfy $(m-2)/2 \le n-1$, so the highest-order truncation term that can be canceled is of order $m = 2n$. In some embodiments, the system may instead cancel a different number of truncation terms.

Thus, the system can cancel all the truncation terms up to the order of 2n when the Laplacian estimate is calculated as the linear combination of equations representing differences of potentials from each of the n rings and the central disc. In particular, these equations may range from equation (2) for innermost concentric ring 304 up to equation (3) for the nth and outermost concentric ring 308. The null space vector $\bar{x}$ can be used as the coefficients of the respective potential differences, and the resulting linear combination can be solved for the NDM estimate of the Laplacian $\Delta v_0$:

$$\Delta v_0 \cong \frac{4}{r^2(x_1 + \ldots + n^2 x_n)} \qquad (6)$$

$$\left[ x_1 \left( \frac{1}{2\pi} \int_0^{2\pi} v(r, \theta) d\theta - v_0 \right) + \ldots + x_n \left( \frac{1}{2\pi} \int_0^{2\pi} v(nr, \theta) d\theta - v_0 \right) \right]$$

In an example of a TCRE with equal inter-ring separations, the coefficients determined in this manner may be substantially equal to $2^4 = 16$ for the difference of the inner ring's potential from the central disc potential, and $-1$ for the difference of the outer ring's potential from the central disc potential.

In some embodiments, this Laplacian estimate signal may be calculated using a custom preamplifier board, and may be the only signal sent to the clinical amplifier for each CRE. Alternatively, the Laplacian estimate may be calculated via a special- or general-purpose circuit or computer, a software module, or any other device, and is not limited by the present disclosure.

B. Increasing or Decreasing Inter-Ring Separations

Figure 3B:
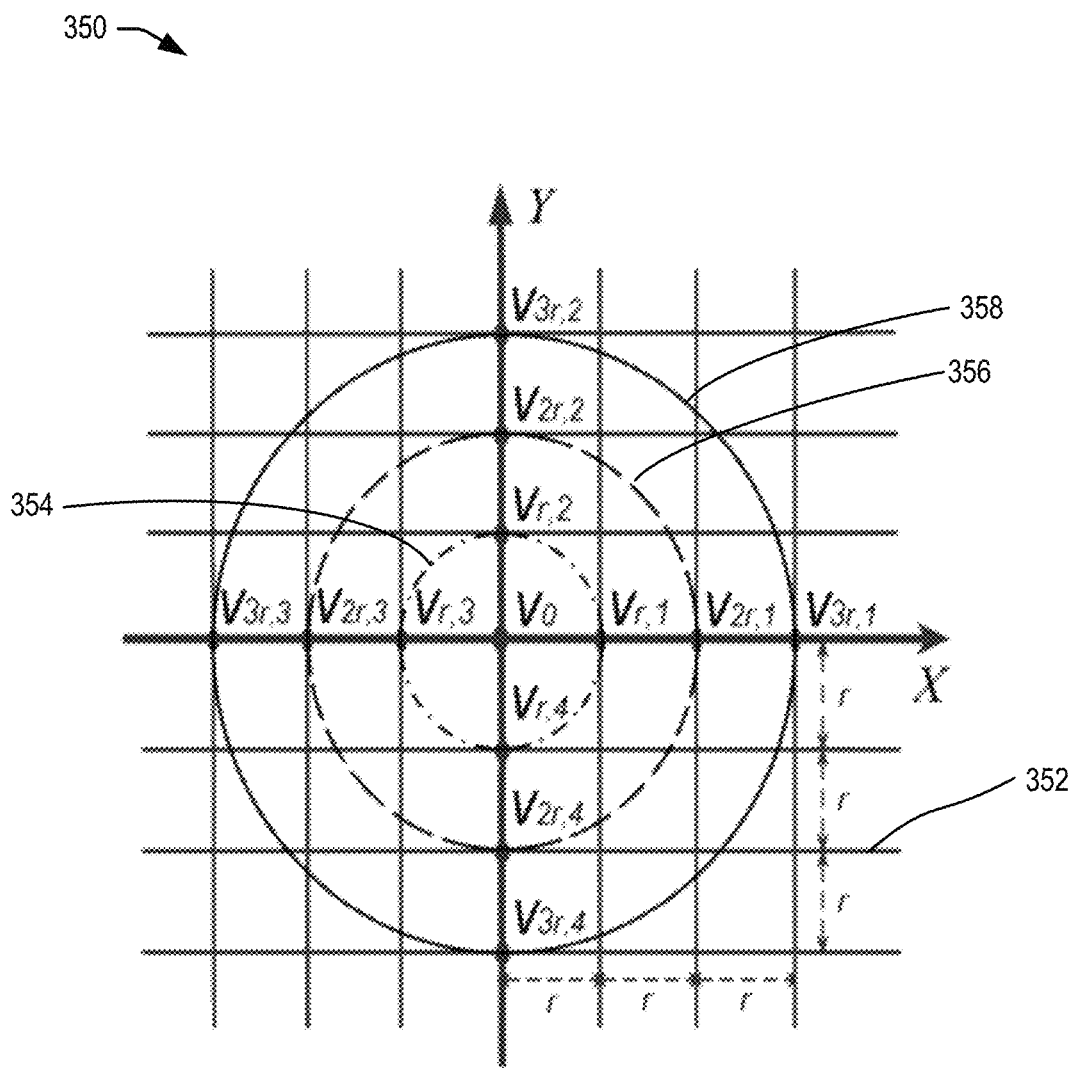
FIG. 3B illustrates an example geometry of a CRE with increasing or decreasing inter-ring separations, according to embodiments.

FIG. 3B illustrates an example geometry of a CRE 350 with increasing or decreasing inter-ring separations, according to embodiments. In this example, CRE 350 is again illustrated on a regular square grid 352, with all inter-point distances equal to r. CRE 350 may have concentric rings that are not spaced with regular intervals or separations between them.

In an embodiment, the inter-ring separation may increase linearly, or according to an arithmetic sequence, for subsequent concentric rings (i.e., the larger a respective ring's radius, the greater the respective ring's radial separation from its neighboring rings). For example, CRE 350 may be a tripolar (n=2) CRE with an inner ring 354 of radius r, and outer ring 358, of radius 3r. In this example, the inter-ring separations are not uniformly equal to r, but rather can increase by r for each subsequent ring.

In some embodiments, the inter-ring separation may decrease linearly for subsequent concentric rings (i.e., the larger a respective ring's radius, the smaller its radial separation from its neighbors). In a second example, CRE 350 may instead be a tripolar (n=2) CRE with an inner ring 356 of radius 2r, and outer ring 358, of radius 3r. In this example, the inter-ring separations are not uniformly equal to r, but rather can decrease by r for each subsequent ring.

Accordingly, in some embodiments, the system can use a modified NDM to accommodate CRE configurations with variable inter-ring separations, such as CRE 350. In a typical example, the NDM may estimate a potential Laplacian for inter-ring separations increasing linearly, such as rings 354 and 358, or decreasing linearly, such as rings 356 and 358. Note that in some embodiments, the system can optimize coefficients and/or geometry for CREs with other ring radii configurations besides linearly increasing or decreasing inter-ring separations, as will be described further below.

In particular, for the case of linear increase, the ring radii may increase according to the triangular number sequence:

$$r_j = r_0 + a \frac{j(j+1)}{2}$$

so that the separations between adjacent radii are $r_{j+1} - r_j = (j+1)a$, where $r_j$ is the radius of the jth ring from the center, and a may be a positive constant. For the case of linearly decreasing separations, the ring radii may increase more slowly, according to $$r_j = r_0 + a \frac{j(2n - j + 1)}{2}$$

so that the separations decrease linearly from $r_1 - r_0 = n\alpha$, to $r_n - r_{n-1} = \alpha$, in increments $r_{j+1} - r_j = (n-j)\alpha$.

Thus, in either the case of linearly increasing or decreasing inter-ring separations, the radius of outermost ring 358 (or alternatively, the sum of all the inter-ring separations to ring 358) may be calculated using the formula for the nth term of the triangular number sequence:

$$r_n - r_0 \propto \frac{n(n+1)}{2}.$$

Accordingly, the matrix A of truncation term coefficients $I^{2(k+1)}$ from equation (4) may be modified to A' for the case of CREs with linearly increasing inter-ring separations, and A″ for the case of linearly decreasing separations, respectively:

$$A' = \begin{pmatrix} 1 & 3^4 & \cdots & \left(\frac{n(n+1)}{2}\right)^4 \\ 1 & 3^6 & \cdots & \left(\frac{n(n+1)}{2}\right)^6 \\ \vdots & \vdots & \ddots & \vdots \\ 1 & 3^n & \cdots & \left(\frac{n(n+1)}{2}\right)^{2n} \end{pmatrix} \quad (7)$$

$$A'' = \begin{pmatrix} n^4 & (2n-1)^4 & \cdots & \left(\frac{n(n+1)}{2}\right)^4 \\ n^6 & *(2n-1)^6 & \cdots & \left(\frac{n(n+1)}{2}\right)^6 \\ \vdots & \vdots & \ddots & \vdots \\ n^{2n} & (2n-1)^{2n} & \cdots & \left(\frac{n(n+1)}{2}\right)^{2n} \end{pmatrix} \quad (8)$$

Note that for the example of constant inter-ring separations, the (k, l)th element of matrix A in equation (4) is given by $A_{kl}=l^{2(k+1)}$, where ring radius multiplier l may be equal to the radius of the lth ring in units of r. Here r is the radius of innermost ring 304 and is the unit of grid 302 in the example of FIG. 3A, and of grid 352 in the example of FIG. 3B. In the present example, the inter-ring separations grow or decrease arithmetically, so the ring radius multiplier l may be adjusted to account for this. For example, for arithmetically growing separations, the lth ring may have radius $$r_l = \frac{l(l+1)}{2}r$$

(according to the triangular number sequence) instead of lr, so $$A'_{kl} = \left(\frac{l(l+1)}{2}\right)^{2(k+1)}.$$

For the case of arithmetically decreasing separations, the lth ring may have radius $$r_l = \frac{l(2n-l+1)}{2}r$$

(according to the triangular number sequence) instead of lr, so $$A''_{kl} = \left(\frac{l(2n-l+1)}{2}\right)^{2(k+1)}.$$

The system can solve for the null space of these matrices, and use the computed null space as coefficients to estimate the Laplacian. The null space may again be rescaled by an arbitrary constant factor. In an example of a TCRE with decreasing inter-ring separations, such that the inner ring radius is approximately 0.62 times the outer ring radius, the coefficients determined in this manner may be substantially equal to 7 for the difference of the inner ring's potential from the central disc potential, and −1 for the difference of the outer ring's potential from the central disc potential. Equivalently, the first coefficient may be substantially equal to −7 times the second coefficient. In another example, the ratio of the coefficients may be in a range, such as between −8 and −6.

II. Optimizing CRE Radii

In some embodiments, the system can optimize the linear combination coefficients and/or the ring radii for CREs having other arrangements of variable inter-ring separations, including nonlinear ones. For example, the inter-ring separation variations need not change monotonically. In some embodiments, the system can continue to modify matrix A in order to estimate the Laplacian, similar to equations (7) and (8) above. Alternatively, the system may instead solve an NDM more generally for arbitrary CRE ring radii and/or geometric configurations. Moreover, the system can optimize the ring radii for a given number of rings, in order to determine a CRE geometry likely to result in the most accurate measurements.

That is, the system may solve a general inter-ring separation optimization problem (or equivalently, a general ring radii optimization problem). In some embodiments, the system solves this optimization problem for the NDM or (4n+1)-point method of Laplacian estimation. Alternatively, the system can use another estimation method, such as a finite dimensions model (FDM), as described below.

In order to solve the generalized optimization problem, the system may first determine a truncation term coefficient function for the CRE. In particular, as described above, the disclosed system and methods can cancel the Taylor series truncation terms up to the order of 2n, i.e. $O(r^{2n})$. The remaining non-canceled $O(r^{2n+2})$ terms in the Taylor expansion may also be referred to as truncation terms, or as non-canceled truncation terms.

As discussed above, the (k, l)th element of matrix A may be given by $A_{kl}=l^{2(k+1)}$, where ring radius multiplier l may be equal to the radius of the lth ring in units of the innermost ring radius, r. In the non-linear case, the lth ring may have a general radius value $r_l$, so the matrix elements of A may be given by $A_{kl}=(r_l/r)^{2(k+1)}$. Accordingly, the system may determine expressions for a set of multiplicative prefactors or coefficients $c^{CRE}(\alpha,k)$ associated with such remaining non-canceled truncation terms, where k is the order of a respective truncation term. In particular, the system may determine such truncation term coefficients $c^{CRE}$ as functions of these ring radius multipliers or normalized radii $r_l/r$. The system may thus solve the general optimization problem by determining the values of $r_l$ (or, equivalently, of the ratio $r_l/r$) that minimize the absolute value of a truncation term, such as the nonzero or non-canceled truncation term of lowest order k.

In particular, the system may solve such a general optimization problem for tripolar CRE (TCRE; n=2) and quadripolar CRE (QCRE; n=3) configurations, as described herein below. In some embodiments, the system can optimize CREs with other numbers of rings, or can optimize other characteristics of the CRE geometry besides the ring radii, and is not limited by the present disclosure. Note that, in this example, $c^{CRE}(\alpha,k)$ represents the kth-order coefficients as a function of all the ring radius multipliers or normalized radii $r_l/r$, as well as k. For example, for the TCRE (n=2) configuration, $c_{TCRE}(\alpha,k)$ can be a function of the innermost ring ratio $\alpha$. Likewise, for the QCRE (n=3) configuration, $c^{QCRE}(\alpha, \beta, k)$ can be a function of both the innermost ring ratio $\alpha$ and the middle ring ratio $\beta$.

Note also that in various embodiments, the system may use the ring radius multiplier l as the radius of the lth ring in units of any ring in the CRE. For example, the ring radius multiplier l may equal the radius of the lth ring in units of the innermost ring radius, or in units of the outermost ring radius. In another example, the ring radius multiplier l may equal the radius of the lth ring divided by the radius of any other ring. In some embodiments, the respective radius may instead be divided by a constant, or may not be divided by anything. While this choice may affect the elements of A, the null space vector of matrix A may be insensitive to such a choice, and therefore the coefficients used to compute the Laplacian may be insensitive to this choice. In particular, the null space vector may be independent of this choice, within a possible overall normalization factor.

A. Truncation Term Coefficient Function for the TCRE Configuration

First, consider a TCRE (n=2), such as TCRE 200 in FIG. 2A, using the NDM. Assuming, as in the example of FIG. 2A, that the TCRE has two rings with radii $\alpha r$ and r, where the dimensionless coefficient $\alpha$ satisfies $0<\alpha<1$, for each ring the integral of the Taylor series can be taken along a circle with the corresponding radius. For the outer ring with radius r, the result is equation (2), while for the inner ring with radius $\alpha r$ the result is:

$$\frac{1}{2\pi}\int_0^{2\pi} v(\alpha r, \theta)d\theta = \qquad (9)$$

$$v_0 + \frac{(\alpha r)^2}{4}\Delta v_0 + \frac{(\alpha r)^4}{4!}\int_0^{2\pi}\sum_{j=0}^{4}\sin^{4-j}(\theta)\cos^j(\theta)d\theta\left(\frac{d^4 v}{dx^{4-j}dy^j}\right) +$$

$$\frac{(\alpha r)^6}{6!}\int_0^{2\pi}\sum_{j=0}^{6}\sin^{6-j}(\theta)\cos^j(\theta)d\theta\left(\frac{d^6 v}{dx^{6-j}dy^j}\right) + \ldots$$

For this generalized TCRE arrangement, the matrix A of truncation term coefficients $l^k$ from equation (4) may be modified to:

$$A^{TCRE}=(\alpha^4 1^4)=(\alpha^4 1) \qquad (10)$$

Accordingly, the null space $\bar{x}^{TCRE}$ of $A^{TCRE}$ may be chosen equal to:

$$\bar{x}^{TCRE} = \left(-\frac{1}{\alpha^4}, 1\right). \qquad (11)$$

Note that null space vectors such as $\bar{x}^{TCRE}$ in equation (11) are not unique, but can be multiplied by arbitrary constant factors. In particular, for any vector $\bar{x}^{TCRE}$ that belongs to the null space of matrix $A^{TCRE}$ and a constant factor c, the rescaled vector $c\bar{x}^{TCRE}$ also belongs to the null space of matrix $A^{TCRE}$ because $A^{TCRE}(c\bar{x}^{TCRE})=c(A^{TCRE}\bar{x}^{TCRE})=c\bar{0}=\bar{0}$. Note that such rescaling may not affect the Laplacian on the left-hand side of equation (6), because the coefficients appear in both the numerator and denominator on the right-hand side of equation (6).

In some embodiments, the Laplacian may instead be estimated without regard to the factor $$\frac{4}{r^2(x_1 + \cdots + n^2 x_n)}$$

on the right-hand side of equation (6), i.e. the Laplacian estimate may be computed in arbitrary units, or with an arbitrary overall normalization. In some embodiments, the Laplacian estimate may undergo signal processing, such as filtering, demeaning, etc. The output of such signal processing may result in a Laplacian estimate scaled to an amplitude range required for a specific application, and therefore may not be sensitive to overall constant factors in the set of coefficients.

Equations (9) and (2) can be linearly combined using the null space vector $\bar{x}^{TCRE}$ from equation (11) as coefficients. That is, the system may multiply equation (9) by $-1/\alpha^4$, multiply equation (2) by 1, and add the two resulting products together. The system may further solve the sum for the Laplacian $\Delta v_0$:

$$\Delta v_0 = \frac{4}{r^2\left(1 - \frac{1}{\alpha^2}\right)}\left[-\frac{1}{\alpha^4}(v_{MR} - v_0) + (v_{OR} - v_0) + \sum_{k=6,8,\ldots}^{\infty}\frac{(1-\alpha^{k-4})r^k}{k!}\int_0^{2\pi}\sum_{j=0}^{k}\sin^{k-j}(\theta)\cos^j(\theta)d\theta\left(\frac{\partial^k v}{\partial x^{k-j}\partial y^j}\right)\right] \qquad (12)$$

$$\text{where } v_{MR} = \frac{1}{2\pi}\int_0^{2\pi}v(\alpha r, \theta)d\theta$$

is the potential on the middle ring (e.g., ring 204 of the example of FIG. 2A) with radius $\alpha r$ and $$v_{OR} = \frac{1}{2\pi}\int_0^{2\pi}v(r, \theta)d\theta$$

is the potential on the outer ring (e.g., ring 206 of the example of FIG. 2A) with radius r.

As described above, because the odd-order truncation terms may vanish due to integration over the circle, the system can use n equations for n rings to cancel the even-order truncation terms up to order 2n. In this example, n=2 for the TCRE, so the Laplacian estimate from equation (12) allows cancellation of the truncation terms up to order 2n=4. Accordingly, the truncation term coefficients $c^{TCRE}(\alpha, k)$ may be expressed as functions of the inner ring radius $\alpha$ and the non-canceled truncation term order k, i.e. for even k≥6. After simplification, the coefficients $c^{TCRE}(\alpha, k)$ of truncation terms with the general form $$\frac{c^{TCRE}(\alpha, k)r^{k-2}}{k!}\int_0^{2\pi}\sum_{j=1}^{k}\sin^{k-j}(\theta)\cos^j(\theta)d\theta\left(\frac{\partial^k v}{\partial x^{k-j}\partial y^j}\right)$$

may be expressed as:

$$c^{TCRE}(\alpha, k) = \frac{4(\alpha^4 - \alpha^k)}{\alpha^2(\alpha^2 - 1)} \qquad (13)$$

for even k≥6. Note that the expression of equation (13) for the truncation term coefficients $c^{TCRE}(\alpha, k)$ depend on $\alpha$ both indirectly through the weighting coefficients of equation (11) used to combine the CRE measurements into a Laplacian estimate, and directly through the CRE's geometry via equations (2) and (9).

The system may use a $5^{th}$ percentile (corresponding to the absolute value of the truncation term coefficient equal to 0.2) to determine a boundary value of $\alpha$ for the lowest non-canceled truncation term (of order 2n+2=6). In this example, the resulting boundary value indicates $\alpha$=0.22. Accordingly, an optimal range of the concentric ring radius $\alpha r$, keeping absolute values of the sixth-order truncation term coefficients within the $5^{th}$ percentile, may be determined according to the inequality $0<\alpha\leq 0.22$.

B. Truncation Term Coefficient Function for the QCRE Configuration

Next, consider a QCRE (n=3), such as TCRE 250 in FIG. 2B, using the NDM. Assuming, as in FIG. 2B, that the QCRE has three rings with radii $\alpha r$, $\beta r$, and r where coefficients $\alpha$ and $\beta$ satisfy $0<\alpha<\beta<1$, for each ring the integral of the Taylor series may be taken around a circle with the corresponding radius. For the outermost ring (e.g., ring 258 in FIG. 2B) with radius r, the result is equation (2), for the innermost ring (e.g., ring 254 in FIG. 2B) with radius $\alpha r$ the result is equation (9), and for the middle ring (e.g., ring 256 in FIG. 2B) with radius $\beta r$ the result is:

$$\frac{1}{2\pi}\int_0^{2\pi} v(\beta r, \theta)d\theta = \qquad (14)$$

$$v_0 + \frac{(\beta r)^2}{4}\Delta v_0 + \frac{(\beta r)^4}{4!}\int_0^{2\pi}\sum_{j=0}^{4}\sin^{4-j}(\theta)\cos^j(\theta)d\theta\left(\frac{d^4 v}{dx^{4-j}dy^j}\right) +$$

$$\frac{(\beta r)^6}{6!}\int_0^{2\pi}\sum_{j=0}^{6}\sin^{6-j}(\theta)\cos^j(\theta)d\theta\left(\frac{d^6 v}{dx^{6-j}dy^j}\right) + \ldots$$

For this generalized QCRE arrangement, the matrix A of truncation term coefficients r from equation (4) may be modified to:

$$A^{QCRE} = \begin{pmatrix} \alpha^4 & \beta^4 & 1^4 \\ \alpha^6 & \beta^6 & 1^6 \end{pmatrix} = \begin{pmatrix} \alpha^4 & \beta^4 & 1 \\ \alpha^6 & \beta^6 & 1 \end{pmatrix} \qquad (15)$$

Accordingly, the null space $\overline{x}^{QCRE}$ of $A^{QCRE}$ may be chosen equal to:

$$\overline{x}^{QCRE} = \left(-\frac{1-\beta^2}{\alpha^4(\alpha^2-\beta^2)}, -\frac{\alpha^2-1}{\beta^4(\alpha^2-\beta^2)}, 1\right) \qquad (16)$$

In this example, the null space $\overline{x}^{QCRE}$ may again be rescaled by an arbitrary constant factor.

Equations (9), (14), and (2) can be linearly combined using the null space vector$^{7\iota}$ from equation (16) as coefficients. In particular, the system can multiply equation (9) by $$-\frac{1-\beta^2}{\alpha^4(\alpha^2-\beta^2)},$$

multiply equation (14) by $$-\frac{\alpha^2-1}{\beta^4(\alpha^2-\beta^2)},$$

multiply equation (2) by 1, and add together the three resulting products. The system can solve the sum for the Laplacian $\Delta v_0$.

In this example, 2n=6 for n=3, accordingly the system can cancel the fourth- and sixth-order truncation terms. After simplification, the coefficients $c^{QCRE}(\alpha, \beta, k)$ of truncation terms with the general form $$\frac{c^{QCRE}(\alpha, \beta, k)r^{k-2}}{k!}\int_0^{2\pi}\sum_{j=0}^{k}\sin^{k-j}(\theta)\cos^j(\theta)d\theta\left(\frac{\partial^k v}{\partial x^{k-j}\partial y^j}\right)$$

can be expressed as the function of coefficients $\alpha$ and $\beta$ and the truncation term order k for even $k\geq 8$:

$$c^{QCRE}(\alpha, \beta, k) = \frac{4[\alpha^k\beta^4(\beta^2-1) + \alpha^6(\beta^4-\beta^k) + \alpha^4(\beta^k-\beta^6)]}{\alpha^2\beta^2(\alpha^2-1)(\beta^2-1)(\alpha^2-\beta^2)}. \qquad (17)$$

Note that the expression of equation (17) for the truncation term coefficients $c^{QCRE}(\alpha, \beta, k)$ depend on the radii $\alpha$ and $\beta$ both indirectly through the weighting coefficients of equation (16) used to combine the CRE measurements into a Laplacian estimate, and directly through the CRE's geometry via equations (2), (9), and (14).

The system may use a $5^{th}$ percentile (corresponding to the absolute value of the truncation term coefficient equal to 0.19) to determine boundary values of $\alpha$ and $\beta$, which keeps absolute values of the for the lowest non-canceled truncation term coefficients (of order 2n+2=8) within the $5^{th}$ percentile. Accordingly, the optimal range of concentric ring radii $\alpha r$ and $\beta r$, keeping absolute values of the eighth-order truncation term coefficients within the $5^{th}$ percentile, may be determined by the inequalities $0<\alpha<\beta<1$ and $\alpha<0.21/\beta$ or, equivalently, $\alpha\beta\leq 0.21$.

C. General Inter-Ring Separations Optimization Problem and its Constraints

To determine optimized ring radii, the system can solve a constrained optimization problem to minimize the discrepancy between the Laplacian estimate and the full Taylor expansion. As discussed previously, the system may use n equations (representing differences of the potentials on the n rings and the potential $v_0$ on the central disc of the CRE) to estimate the Laplacian in terms of a Taylor expansion with n even-order truncation terms canceled (i.e., up to order 2n).

More broadly, cancellation of the truncation terms up to order 2n characterizes the amount of information about the Laplacian that may be obtained from the total of n+1 recording sites. That is, given that the n+1 recording sites are only capable of measuring a total of n+1 potentials (or n potential differences), the system can only characterize the potential and/or its Laplacian with finite accuracy. Accordingly, the NDM described above can linearly combine these measurements so as to cancel as many low-order truncation terms as possible. As discussed previously, the more truncation terms canceled, the more accurate the Laplacian estimate is likely to be.

However, in optimizing the ring radii (or other aspects of CRE geometry), the system can take advantage of further freedom to adjust the locations of the rings, and thereby further reduce the measurement error of the potential's Laplacian. In an embodiment, the system does so by minimizing the absolute value of the lowest non-canceled truncation term or terms. Accordingly, the system may minimize the absolute values of truncation term coefficients for TCRE and QCRE configurations, using the functions $c^{TCRE}(\alpha, k)$ from equation (13) and $c^{QCRE}(\alpha, \beta, k)$ from equation (17), respectively. Formal definitions of the optimization problem for the TCRE and QCRE configurations are $$\min_{0<\alpha<1} |c^{TCRE}(\alpha, 6)| \text{ and } \min_{0<\alpha<\beta<1} |c^{QCRE}(\alpha, \beta, 8)|$$

respectively.

Solving this optimization problem may result in TCRE and QCRE designs with optimized inter-ring separations that minimize the truncation error and, therefore, maximize the accuracy of surface Laplacian estimates.

In an embodiment, the system minimizes absolute values of truncation term coefficients for this optimization. Note that the signs of the truncation term coefficients have been shown to be consistent for both constant and variable inter-ring separations CRE configurations. Specifically, the signs of the truncation term coefficients may all be negative for TCREs, and all be positive for QCREs. Thus, for both configurations, the truncation terms may reinforce one another, i.e. larger absolute values of truncation term coefficients may reliably result in a larger overall truncation error. In an embodiment, the optimization problem is solved for the lowest nonzero truncation term order, equal to 6 and 8 for TCRE and QCRE configurations, respectively. These lowest non-canceled truncation terms may be minimized because they are likely to contribute most strongly to the truncation error.

Note that the expressions of equations (13) and (17) for the truncation term coefficients $c^{TCRE}(\alpha, k)$ and $c^{QCRE}(\alpha, \beta, k)$ depend on the radii $\alpha$ and $\beta$ both indirectly through the weighting coefficients, and directly through the CRE's geometry. Thus, the system may globally optimize the radii by considering both the freedom to combine measured potentials by weighting and the freedom to modify the CRE geometry simultaneously. Alternatively, in some embodiments, the system can instead perform optimization that optimizes these degrees of freedom separately, or only considers one of them, and is not limited by the present disclosure.

In an embodiment, the system uses an algorithm for finding a global solution to this constrained optimization problem based on using the 5$^{th}$ percentile of the truncation term coefficients. That is, the algorithm can be based on determining boundary values separating the lowest 5% from the highest 95% of the absolute values of truncation term coefficients. Accordingly, the system can determine a range of optimal separations between the central disc and the concentric rings to be used in the optimized TCRE and QCRE designs based on the absolute values of the truncation term coefficients being within such a 5$^{th}$ percentile. In some embodiments, a 10$^{th}$ percentile, or other percentiles can be used, such as a 15$^{th}$ percentile, 20$^{th}$ percentile, or any other percentile value, and are not limited by the present disclosure.

III. Accounting for Ring Width and Disc Area Via Finite Dimensions Model (FDM)

In the negligible dimensions model (NDM) example of FIG. 3A, the central disc of the CRE is represented as a point with negligible radius and the concentric rings are represented as circles with negligible widths. However, in some embodiments, the system can account for ring widths and disc area via a finite dimensions model (FDM). In particular, the system can implement the FDM by averaging the Taylor expansion of the potential over regions that span or sample the areas of the central disc and/or the rings, as disclosed herein. In an embodiment, the regions may be a plurality of circles. In various embodiments, the FDM can be used together with, and/or combined with, any of the other methods described herein. For example, in some embodiments, the FDM may be used to optimize the weighting coefficients for Laplacian estimation and/or to optimize the ring radii or other geometrical characteristics of a CRE.

Similarly to the NDM, the FDM can proceed by averaging the potential over a plurality of points, including averaging around circles, in order to obtain an estimate of the Laplacian in terms of a Taylor expansion. Further, as in the NDM, the system can solve for a null space in order to cancel Taylor expansion truncation terms and/or optimize a CRE's ring radii so as to minimize a non-canceled truncation term. However, unlike the case of the NDM, in the FDM, the system can average over regions spanning finite areas of the recording sites, such as finite widths of the concentric rings.

Figure 4:
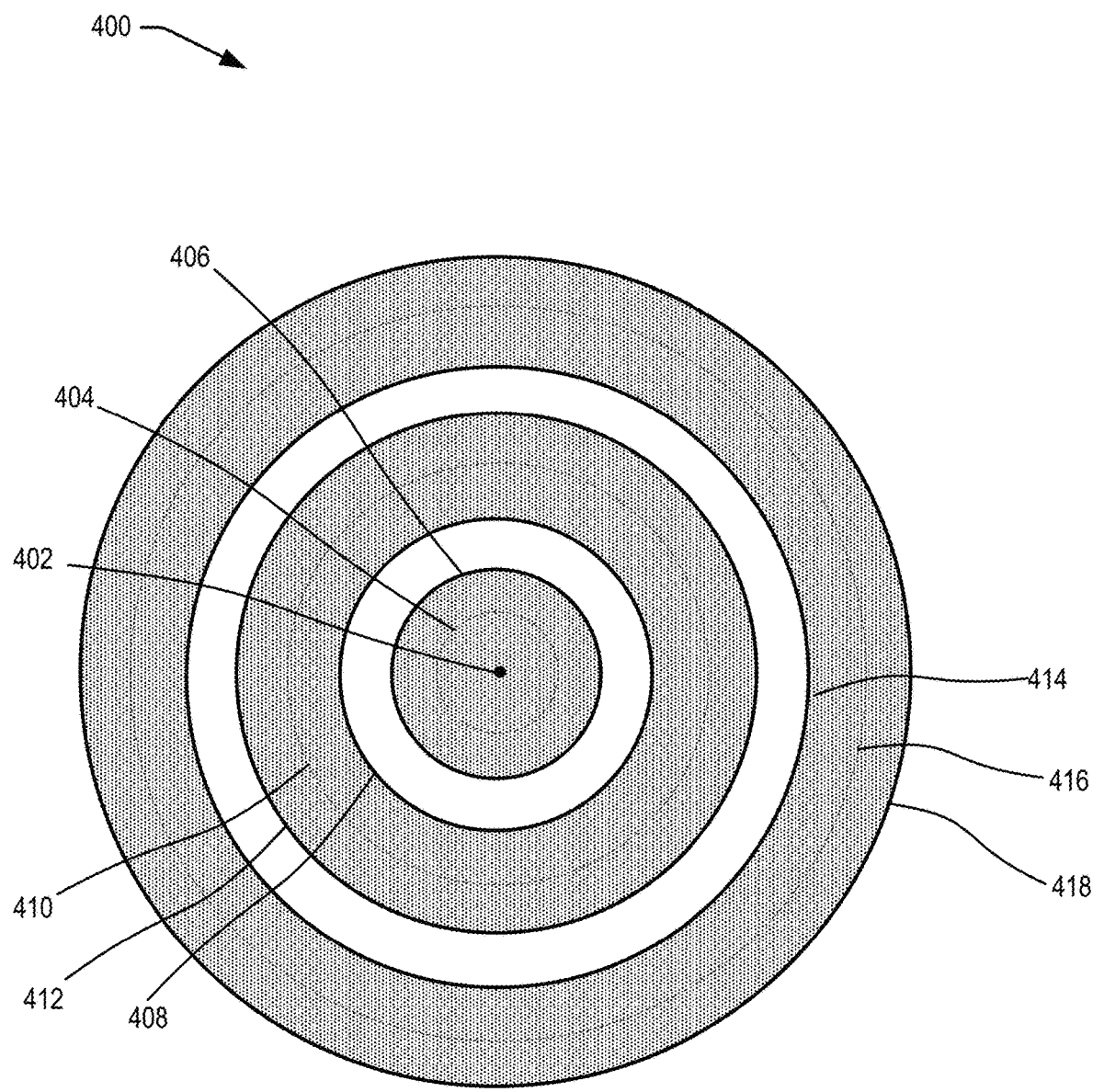
FIG. 4 illustrates accounting for non-negligible central disc radius and ring widths of an example CRE, according to embodiments.

FIG. 4 illustrates accounting for non-negligible central disc radius and ring widths of an example CRE 400 via an FDM, according to embodiments. In this example configuration, the central disc has a radius of 2r and both concentric rings have widths of 2r. As a result, the inner ring ranges from a radius of 3r to 5r, and the outer ring ranges from radius of 6r to 8r. In this example, the system averages the Taylor expansion of the potential over a plurality of circles sampling the areas of the central disc and the rings. Note that, in some embodiments, the system can optimize coefficients and/or geometrical parameters for different CRE configurations, such as for CREs with variable-width and/or variable-radius rings, and is not limited by the present disclosure.

TABLE 1

| Circle radius | Average potential on circle | Taylor series for circle |
|---|---|---|
| r | $v_r = \frac{1}{4}\sum_{i=1}^{4} v_{r,i}$ | $v_r \cong v_0 + \frac{2 \cdot 1^2}{4 \cdot 2!}r^2 \Delta v_0 + \frac{2 \cdot 1^4}{4 \cdot 4!}r^4 T_4$ |
| 2r | $v_{2r} = \frac{1}{4}\sum_{i=1}^{4} v_{2r,i}$ | $v_{2r} \cong v_0 + \frac{2 \cdot 2^2}{4 \cdot 2!}r^2 \Delta v_0 + \frac{2 \cdot 2^4}{4 \cdot 4!}r^4 T_4$ |
| 3r | $v_{3r} = \frac{1}{4}\sum_{i=1}^{4} v_{3r,i}$ | $v_{3r} \cong v_0 + \frac{2 \cdot 3^2}{4 \cdot 2!}r^2 \Delta v_0 + \frac{2 \cdot 3^4}{4 \cdot 4!}r^4 T_4$ |
| 4r | $v_{4r} = \frac{1}{4}\sum_{i=1}^{4} v_{4r,i}$ | $v_{4r} \cong v_0 + \frac{2 \cdot 4^2}{4 \cdot 2!}r^2 \Delta v_0 + \frac{2 \cdot 4^4}{4 \cdot 4!}r^4 T_4$ |
| 5r | $v_{5r} = \frac{1}{4}\sum_{i=1}^{4} v_{5r,i}$ | $v_{5r} \cong v_0 + \frac{2 \cdot 5^2}{4 \cdot 2!}r^2 \Delta v_0 + \frac{2 \cdot 5^4}{4 \cdot 4!}r^4 T_4$ |

TABLE 1-continued

| Circle radius | Average potential on circle | Taylor series for circle |
|---|---|---|
| 6r | $v_{6r} = \frac{1}{4}\sum_{i=1}^{4} v_{6r,i}$ | $v_{6r} \cong v_0 + \frac{2 \cdot 6^2}{4 \cdot 2!} r^2 \Delta v_0 + \frac{2 \cdot 6^4}{4 \cdot 4!} r^4 T_4$ |
| 7r | $v_{7r} = \frac{1}{4}\sum_{i=1}^{4} v_{7r,i}$ | $v_{7r} \cong v_0 + \frac{2 \cdot 7^2}{4 \cdot 2!} r^2 \Delta v_0 + \frac{2 \cdot 7^4}{4 \cdot 4!} r^4 T_4$ |
| 8r | $v_{8r} = \frac{1}{4}\sum_{i=1}^{4} v_{8r,i}$ | $v_{8r} \cong v_0 + \frac{2 \cdot 8^2}{4 \cdot 2!} r^2 \Delta v_0 + \frac{2 \cdot 8^4}{4 \cdot 4!} r^4 T_4$ |

In Table 1, the notation previously used for the NDM method (as in the examples of FIGS. 3A and 3B) is used to describe the average potentials on concentric circles of radii ranging from r to 8r, in order to account for non-negligible ring and disc areas. Note that, as in the previous examples, the potentials on the individual circles can still be averaged and/or integrated around the circles, i.e. circumferentially. In particular, in Table 1, each row corresponds to a single respective circle, but the second column shows the computation of the respective circle's potential as an average around the circle. In this example, four points are averaged, but any number of points can be used, sampled, and/or integrated. In the example of Table 1, $v_{kr,i}$ corresponds to the ith point averaged to compute the potential $v_{kr}$ of the concentric circle with radius kr.

In turn, a number of concentric circles (in this example, three circles) or other regions can be averaged to compute the potential over the area of each respective recording site. For example, point 402 corresponds to the potential $v_0$ at the center of the CRE, $v_r$ corresponds to the potential on circle 404 within the central disc, and $v_{2r}$ corresponds to the potential on circle 406 on the edge of the central disc. Likewise, on the inner ring, $v_{3r}$ corresponds to the potential on circle 408 on the inner edge of the ring, $v_{4r}$ corresponds to the potential on circle 410 in the center of the ring, and $v_{5r}$ corresponds to the potential on circle 412 on the outer edge of the ring. On the outer ring, $v_{6r}$ corresponds to the potential on circle 414 on the inner edge of the ring, $v_{7r}$ corresponds to the potential on circle 416 in the center of the ring, and $v_{8r}$ corresponds to the potential on circle 418 on the outer edge of the ring. In some embodiments, other numbers of points and/or circles can be averaged to compute the potentials, and are not limited by the present disclosure. For example, the circles may be spaced more closely (for example, so that the sum over the circles forms a discrete approximation of an integral over the area of a respective recording site), and/or may be spaced with varying separations between radii.

The third column of Table 1 further shows the solution for these average concentric circle potentials using corresponding FPM Taylor series expansion equations similar to (1). In Table 1, $$T_4 = \frac{\partial^4 v}{\partial x^4} + \frac{\partial^4 v}{\partial y^4}$$

refers to the fourth-order truncation term.

Note that, in some embodiments, the CRE may possess, or approximately possess, cylindrical symmetry, that is, two-dimensional rotational symmetry about the CRE's center. However, the potential measured by the CRE may not necessarily possess such symmetry, in particular because the CRE may measure electrical activity originating from a target without such symmetry, such as a human brain. Accordingly, the point potentials averaged over the area of a respective recording site, for example points distributed around circles 408, 410, or 412, may or may not be equal before averaging. However, averaging around the circles may enable the system to cancel all odd-order truncation terms, as in the case of the NDM.

Note that, in some embodiments, the FDM may further account for electrostatic induction effects in the recording sites, which may be conductors. As a result, charges may rearrange on the surfaces of the recording sites, canceling electric fields within the recording sites, and possibly also modifying the potential v outside the recording sites. Note that this effect may be a relatively small correction compared to the potential v itself. For example, in some embodiments, the potentials on the individual circles (or other regions averaged over) may subsequently be constrained to the averaged values of the potentials on each recording site obtained via the FDM and/or NDM, in order to treat the entire system including the CRE self-consistently. Moreover, note that the potential measured by the CRE is typically produced by an object external to the CRE itself, such as a medical patient, or a patient's brain or heart. In addition, other methods may be used to correct for the CRE's effect on the potential v.

In this example, the highest-order truncation term canceled is the fourth-order term, $T_4$. Note that this is consistent with the NDM (as in the example of FIG. 3A), which allows cancellation of all the Taylor series truncation terms up to the order of 2n. In the present example of a TCRE, n=2.

In order to derive the surface Laplacian estimate for the TCRE configuration 400 in the example of FIG. 4, the system can first calculate the potentials on three recording surfaces of the TCRE: the central disc, the inner concentric ring, and the outer concentric ring. To calculate the potential $v_{CD}$ on the central disc, which has radius 2r, the system can average potential $v_0$ at the center point 402 of the square grid, potential $v_r$ on concentric circle 404 of radius r, and potential $v_{2r}$ on concentric circle 406 of radius 2r:

$$v_{CD} = \frac{v_0 + v_r + v_{2r}}{3} \cong v_0 + \frac{5}{12} r^2 \Delta v_0 + \frac{17}{144} r^4 T_4.$$

Likewise, to calculate the potential $v_{MR}$ on the inner concentric ring of TCRE 400, the system can average the potentials on concentric circles 408, 410, and 412, with radii 3r, 4r, and 5r, respectively, as follows:

$$v_{MR} = \frac{v_{3r} + v_{4r} + v_{5r}}{3} \cong v_0 + \frac{25}{6} r^2 \Delta v_0 + \frac{481}{72} r^4 T_4.$$

Finally, to calculate the potential $v_{OR}$ on the outer ring of the TCRE 400, the system can average the potentials on concentric circles 414, 416, and 418, with radii 6r, 7r, and 8r, respectively, as follows:

$$v_{MR} = \frac{v_{6r} + v_{7r} + v_{8r}}{3} \cong v_0 + \frac{149}{12} r^2 \Delta v_0 + \frac{7793}{144} r^4 T_4.$$

The system can then subtract the potential $v_{CD}$ on the central disc from the potential $v_{MR}$ on the inner concentric ring, in order to cancel out $v_0$:

$$v_{MR} - v_{CD} \cong \frac{15}{4} r^2 \Delta v_0 + \frac{105}{16} r^4 T_4.$$

Similarly, the system can subtract the potential $v_{CD}$ on the central disc from the potential $v_{OR}$ on the outer concentric ring, in order to cancel $v_0$: $v_{OR} - v_{CD} \cong 12 r^2 \Delta v_0 + 54 r^4 T_4$.

Finally, the system can linearly combine these potential differences with weighting coefficients, in order to cancel the fourth-order truncation term $T_4$ and thereby estimate the Laplacian $\Delta v_0$. In an embodiment, the system can compute these coefficients using a simpler method than solving for a null space (as in the NDM), which may potentially be less computationally intensive. The system can find coefficients of the respective Laplacian term and fourth-order truncation term $T_4$ from the potential equation for each recording site. For example, for the central disc, the system can find coefficient $L_{CD}=5/12$ for the Laplacian term and $T_{CD}=17/44$ for the truncation term, because these are the coefficients of $r^2 \Delta v_0$ and $r^4 T_4$, respectively, in the equation for $v_{CD}$. Likewise, for the inner concentric ring, the system can find coefficients $L_{MR}=25/6$ and $T_{MR}=481/72$, and for the outer concentric ring, the system can find coefficient $L_{OR}=149/12$ and $T_{OR}=7793/144$. The system can then find the respective coefficients for differential signals $L_{MR}-L_{CD}=15/4$, $T_{MR}-T_{CD}=105/16$, $L_{OR}-L_{CD}=12$, and $T_{OR}-T_{CD}=54$. The system can then solve for coefficients x and y of a linear combination of these differential signals that ensure that the coefficient of the Laplacian equals 1 and the coefficient of $T_4$ equals 0, i.e. solving for the Laplacian and canceling $T_4$. In this example, solving the equations $(L_{MR}-L_{CD})x+(L_{OR}-L_{CD})y=1$ and $(T_{MR}-T_{CD})x+(T_{OR}-T_{CD})y=0$ yields $x=24/55$ and $y=-7/132$, thereby providing the weighting coefficients for combining the potential differences. In some embodiments, the system may also follow a similar procedure for other numbers of rings. For example, for QCRE (n=3) configuration, the system can solve for coefficients x, y, and z of a linear combination of three differential signals that ensure that the coefficient of the Laplacian equals 1 and the coefficients of $T_4$ and $T_6$ equal to 0, i.e. solving for the Laplacian and canceling $T_4$ and $T_6$, etc.

In some embodiments, these coefficients may instead be obtained as solutions $\bar{x}$ for the null space of a matrix A of ring radius multipliers raised to powers, as in the NDM. For example, the (k, l)th element of A may be given by $A_{kl}=l^{2(k+1)}$, where l is a ring radius multiplier associated with the lth concentric ring. The system may obtain the coefficients $\bar{x}$ by solving for the null space of A, or by another method, and is not limited by the present disclosure.

In the example of Table 1, the system may use coefficients 24/55 for $v_{MR}-v_{CD}$ and −7/132 for $v_{OR}-v_{CD}$:

$$\Delta v_0 \cong \frac{1}{r^2} \left[ \frac{24}{55}(v_{MR} - v_{CD}) - \frac{7}{132}(v_{OR} - v_{CD}) \right] = \frac{1}{7260 r^2} [3168(v_{MR} - v_{CD}) - 385(v_{OR} - v_{CD})].$$

In embodiments where the coefficients are determined by solving for a null space, as in the case of the NDM, all the coefficients may be rescaled by the same constant value. In embodiments where the coefficients are determined via the simpler procedure to set the coefficient of the Laplacian to 1 and the coefficient of at least $T_4$ to 0, as described above, a normalization factor associated with the coefficients may not appear in a denominator of the Laplacian estimate. However, the coefficients may still be rescaled by a constant value, because the Laplacian estimate may undergo signal processing. In particular, the output of such signal processing may result in a Laplacian estimate scaled to an amplitude range required for a specific application, and therefore may not be sensitive to overall constant factors in the set of coefficients.

IV. Processes

FIGS. 5A, 5B, 6A, and 6B illustrate example flow diagrams showing processes 500, 550, 600, and 650 as described herein. The processes 500, 550, 600, and 650 are illustrated as logical flow diagrams, each operation of which represents a sequence of operations that can be implemented in hardware, computer instructions, or a combination thereof. In the context of computer instructions, the operations represent computer-executable instructions stored on one or more computer-readable storage media that, when executed by one or more processors, perform the recited operations. Generally, computer-executable instructions include routines, programs, objects, components, data structures, and the like that perform particular functions or implement particular data types. The order in which the operations are described is not intended to be construed as a limitation, and any number of the described operations can be omitted or combined in any order and/or in parallel to implement the processes.

Additionally, some, any, or all of the processes may be performed under the control of one or more computer systems configured with executable instructions and may be implemented as code (e.g., executable instructions, one or more computer programs, or one or more applications) executing collectively on one or more processors, by hardware, or combinations thereof. As noted above, the code may be stored on a computer-readable storage medium, for example, in the form of a computer program comprising a plurality of instructions executable by one or more processors. The computer-readable storage medium is non-transitory.

A. Process for Determining CRE Radii

Figure 5A:
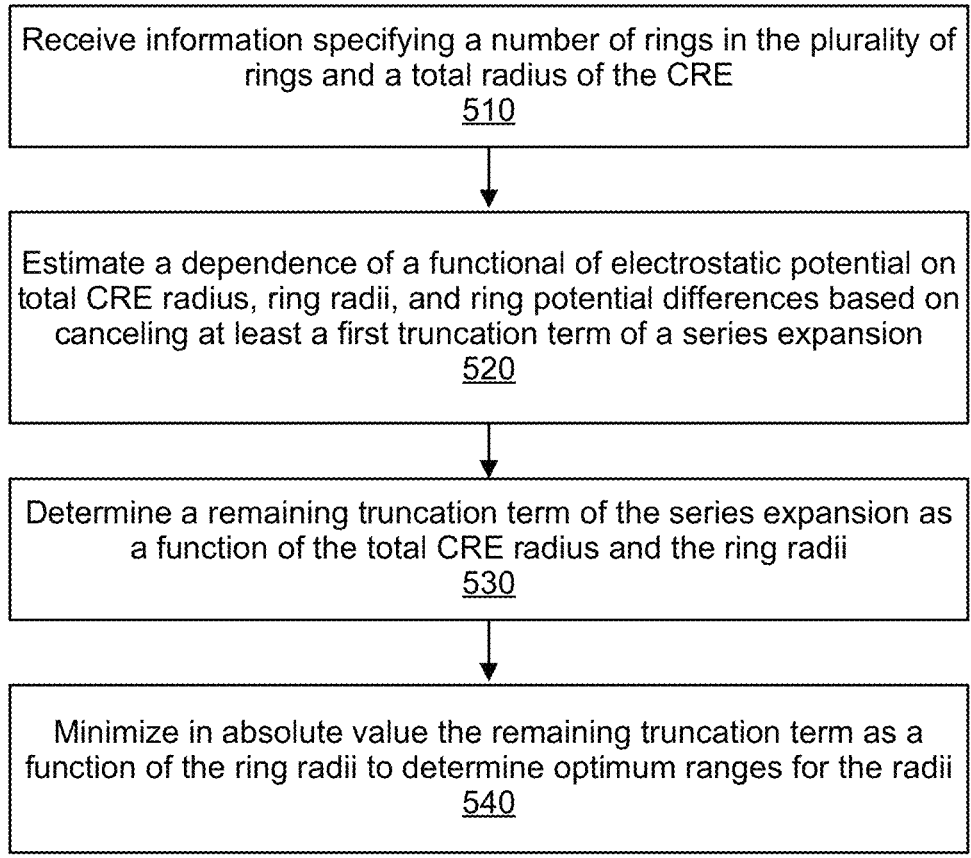
FIG. 5A is a flow chart illustrating an example process for determining values for a set of radii of a plurality of rings of a CRE, according to embodiments.

FIG. 5A is a flow chart illustrating the example process 500 for determining values for a set of radii of a plurality of rings of a CRE, according to embodiments. In some embodiments, process 500 may be performed in a system such as system 1100 of the example of FIG. 11 below or computing device 1004 of FIG. 10B below.

At step 510, the system can receive information specifying a number n of rings in the plurality of rings and a total radius of the CRE. Note that the system can determine values for a set of radii for CREs with any number n of rings. In some embodiments, the system may not explicitly receive the total radius, but may express the optimized ring radii as dimensionless ratios of the total radius, as in the examples of FIGS. 2A and 2B above. In some embodiments, the system may express the ring radii as ratios of another radius, such as the radius of the innermost ring, or the radius of the central disc.

At step 520, the system can estimate a dependence of a functional of the electrostatic potential on the total CRE radius, the ring radii, and ring potential differences based on canceling at least a first truncation term of a series expansion. The potential differences may be differences between the ring potentials measured by the CRE and a potential of the central disc. The first truncation term may have an order 2n. In an embodiment, the system may cancel multiple truncation terms. Typically, this may include n−1 truncation terms of even order, up to the order of 2n. Canceling the first truncation term may involve computing the null space of a matrix based on ring radius multipliers, or dimensionless ratios representing the ring radii, raised to powers.

At step 530, the system can determine a remaining truncation term of the series expansion as a function of the total CRE radius and the ring radii. The remaining truncation term may have a lowest non-canceled order, such as 2n+2, since the truncation terms up to order 2n may be canceled in step 520, and odd-order terms such as order 2n+1 may be canceled by averaging around a circle.

At step 540, the system can minimize in absolute value the remaining truncation term as a function of the ring radii to determine optimum ranges for the radii. In an embodiment, the determined optimum values for the set of radii may optimize a measurement accuracy of the Laplacian of the electrostatic potential by the CRE. The minimization may be based on a percentile value of the remaining truncation term coefficient. For example, the system may find for a TCRE that $0<\alpha \leq 0.22$, or for a QCRE that $0<\alpha<\beta<1$ and $\alpha\beta \leq 0.21$.

B. Process for Forming CRE

Figure 5B:
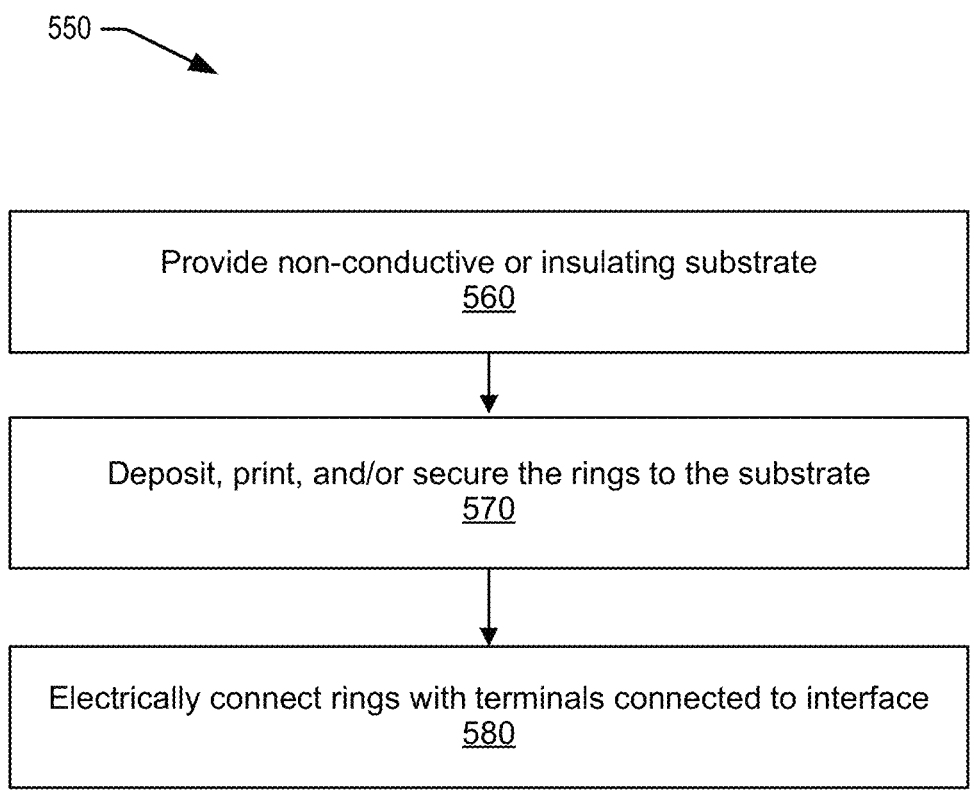
FIG. 5B is a flow chart illustrating an example process for forming a CRE, according to embodiments.

FIG. 5B is a flow chart illustrating an example process 550 for forming a CRE, according to embodiments. In an embodiment, process 500 of FIG. 5A can be used within process 550 for forming a CRE. In particular, forming process 550 may involve generating a set of instructions for forming the CRE based on the ring radii determined via process 500, and further using the generated instructions to form the CRE. In some embodiments, multiple CREs may be formed via the process disclosed herein, for example an array of CREs.

In an embodiment, forming the CRE may involve forming one or more parts of the CRE, such as the ring recording sites, either separately or jointly. In an exemplary embodiment, in step 560, forming process 550 may include providing a non-conductive or insulating substrate. The substrate may be rigid (e.g., gold-plated copper on biocompatible dielectric) or flexible (e.g., polyester film, or silver paste on polyester film) in order to be mounted and/or contact a monitoring target, such as a patient. In an embodiment, the substrate may be designed to provide a consistent contact potential with the target, as well as to fit the target's form. In particular, flexible substrates may improve the CRE's ability to adjust to body contours for better contact and to provide higher signal amplitude and signal-to-noise ratio. In various embodiments, the CRE may be biocompatible, battery-powered, and/or disposable.

In step 570, the process may then include depositing, printing, and/or securing the rings to the substrate. In various embodiments, the rings may be pre-formed, or may be formed on the substrate as part of the forming process. For example, the CRE may be printed via screen printing, inkjet, and/or gravure techniques.

Finally, in step 580, the process may include electrically connecting the rings with terminals that connect to an interface, such as an interface to systems 1000 or 1050 in FIGS. 10A and 10B below. For example, the terminals may be separate leads that can be plugged into an active device. In various embodiments, one or more rings may be shorted together, thereby providing a "quasi-CRE" configuration of a lower number of recording sites. For example, a TCRE with the two rings shorted together may be referred to as a quasi-bipolar CRE. In embodiments of the present disclosure, the CRE design may be optimized by combining signals from all the recording surfaces into a Laplacian estimate. Such an approach may result in higher Laplacian estimation accuracy and radial attenuation.

C. Process for Determining Functional of Potential

Figure 6A:
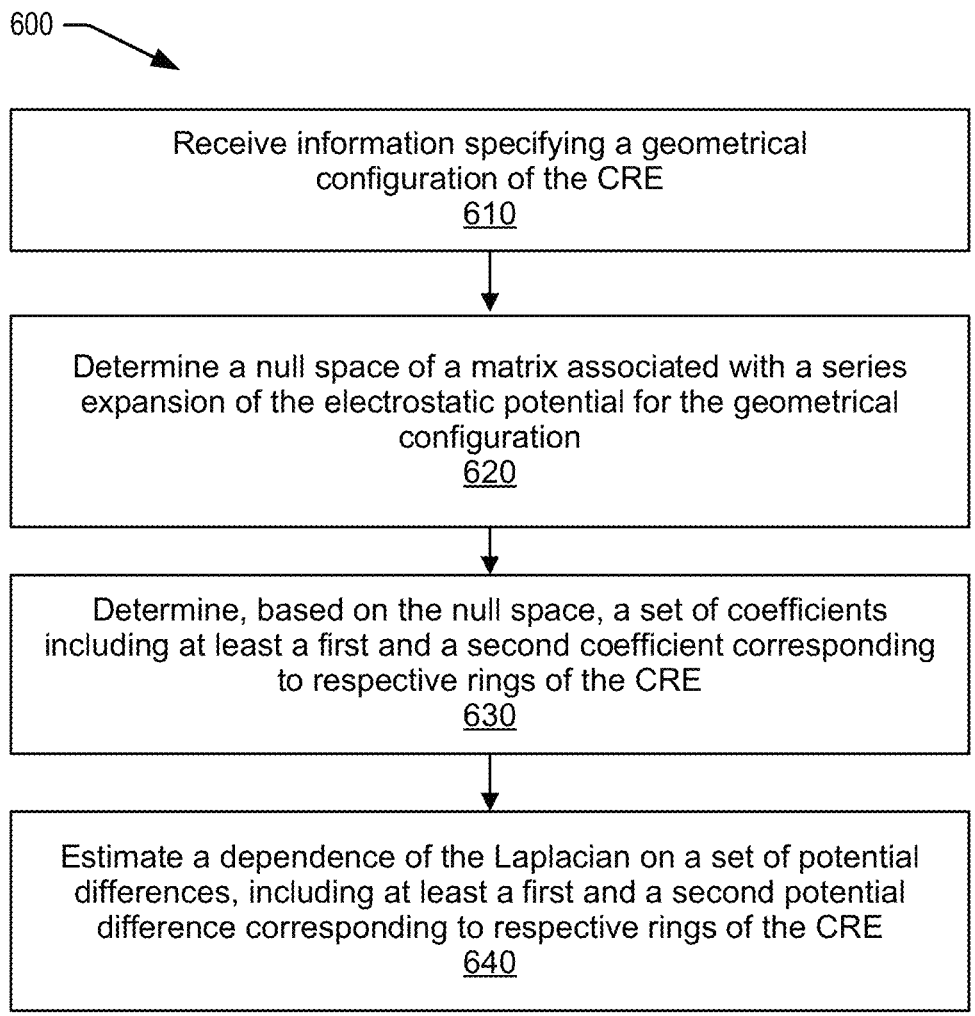
FIG. 6A is a flow chart illustrating an example process for determining a functional of an electrostatic potential measurable by a CRE, according to embodiments.

FIG. 6A is a flow chart illustrating an example process 600 for determining a functional of an electrostatic potential measurable by a CRE, according to embodiments. In some embodiments, process 600 may be performed in a system such as system 1100 of the example of FIG. 11 below or computing device 1004 of FIG. 10B below.

At step 610, the system can receive information specifying a geometrical configuration of the CRE. In a typical example, this may include a number n of rings in the CRE and/or the radii of the rings. In an embodiment, the inter-ring separations may not be uniform. For example, a radius of the outer ring may be different than twice a radius of the inner ring.

At step 620, the system can determine a null space of a matrix associated with a series expansion of the electrostatic potential for the geometrical configuration. Specifically, the system may compute the null space of a matrix based on ring radius multipliers, or dimensionless ratios representing the ring radii, raised to powers. The matrix may have a first dimension equal to a number of rings in the CRE, and a second dimension less than the number of rings in the CRE.

Determining the null space of the matrix may be based on a cancellation of at least a first truncation term of the series expansion of the electrostatic potential. Specifically, the choice of a null space vector may result in the cancellation of the first truncation term. In an embodiment, the matrix is chosen based on this cancellation. The first truncation term may have an order 2n. In an embodiment, the system may cancel multiple truncation terms. Typically, this may include n−1 truncation terms of even order, up to the order of 2n.

At step 630, the system can determine, based on the null space, a set of coefficients including at least a first and a second coefficient corresponding to respective rings of the CRE. For example, for a TCRE with equal inter-ring separations, the coefficients determined may be substantially equal to 16 for the difference of the inner ring's potential from the central disc potential, and −1 for the difference of the outer ring's potential from the central disc potential. In another example, for a TCRE with the inner ring radius approximately 0.62 times the outer ring radius, the coefficients may be substantially equal to 7 for the difference of the inner ring's potential from the central disc potential, and −1 for the difference of the outer ring's potential from the central disc potential. In another example, the ratio of the coefficients may be in a range, for example, between −8 and −6. In various embodiments, the first coefficient is between −10 and 10 times the second coefficient or between −6.5 and −7.5 times the second coefficient. In order to use all the information measured by the recording sites of the TCRE, both coefficients may be nonzero.

At step 640, the system can estimate a dependence of the Laplacian on a set of potential differences, including at least a first and a second potential difference corresponding to respective rings of the CRE. In an embodiment, the system can estimate a dependence of a different functional. In an embodiment, the estimated dependence of the Laplacian may involve a linear combination of the set of potential differences, wherein a respective potential difference is multiplied by a respective coefficient of the set of coefficients.

In some embodiments, the system can further transmit instructions to configure an electrophysiological monitoring system based on the determined set of coefficients. In an embodiment, the system may include an amplification device configured to combine the potential differences measured by the CRE based on the determined coefficients. For example, the system may use a custom preamplifier board to calculate the Laplacian, and this Laplacian estimate may be the only signal sent to the clinical amplifier for each CRE.

D. Process for Estimating Null Space to Determine Optimal Radii

Figure 6B:
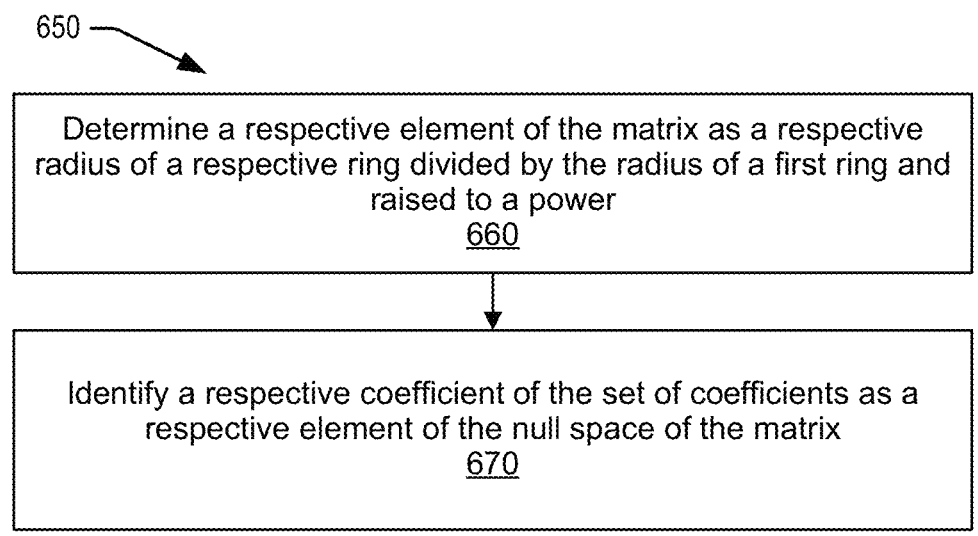
FIG. 6B is a flow chart illustrating an example process for estimating the null space of a matrix to determine optimal values for a set of ring radii of a CRE, according to embodiments.

FIG. 6B is a flow chart illustrating an example process 650 for estimating the null space of a matrix to determine optimal values for a set of ring radii of a CRE, according to embodiments. In some embodiments, process 600 may be performed in a system such as system 1100 of the example of FIG. 11 below or computing device 1004 of FIG. 10B below. Process 650 may provide additional detail of process 600 of FIG. 6A above.

At step 660, the system can determine a respective element of the matrix as a respective radius of a respective ring divided by the radius of a first ring and raised to a power. In a typical example, the first ring would be the outermost ring. In some embodiments, the first ring may instead be another ring (such as an innermost ring, or any other ring), and raised to a power. In some embodiments, the respective radius may instead be divided by a constant, or may not be divided by anything. In particular, the system may use ring radius multipliers, or dimensionless ratios representing the ring radii. In a typical example, the ring radius multiplier may be the ring radius divided by an inner ring radius, an outer ring radius, any other radius, or a constant value.

At step 670, the system can identify a respective coefficient of the set of coefficients as a respective element of the null space of the matrix. In an embodiment, the null space vectors are not unique, but can be multiplied by arbitrary constant factors. In an embodiment, such rescaling may not affect the Laplacian, because the Laplacian estimate may undergo signal processing. In a typical example, such signal processing can include stages such as filtering, demeaning, etc. In particular, the output of such signal processing may result in a Laplacian estimate scaled to an amplitude range required for a specific application, and therefore may not be sensitive to overall constant factors in the set of coefficients. Note also that, in some embodiments, the Laplacian estimate in the FDM may use coefficients obtained by solving for the null space (as described above, e.g., for the NDM). In such embodiments, an overall scale or normalization factor of the coefficients may appear in the denominator of an equation for the Laplacian in terms of the measured potentials, and therefore the Laplacian estimate would be unchanged by rescaling the coefficients (as in the case of the NDM).

V. Example Truncation Term Coefficients

Figure 7:
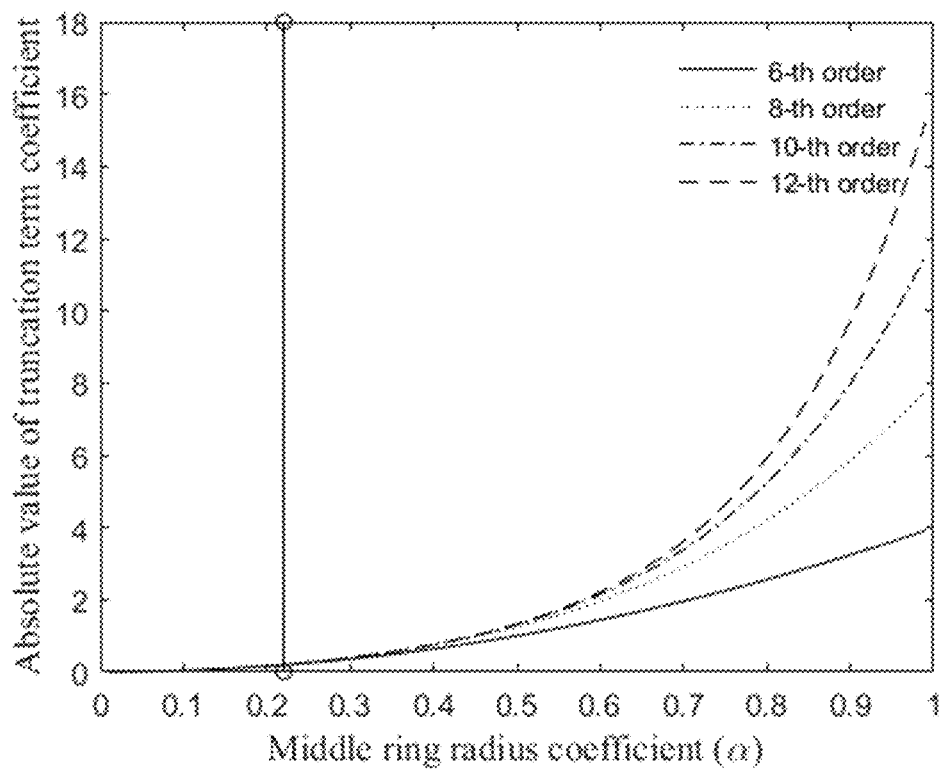
FIG. 7 illustrates the relationship between truncation term coefficients and middle ring radius ratio for a tripolar CRE configuration.

FIG. 7 illustrates the relationship between truncation term coefficients and inner ring radius ratio $\alpha$ for a tripolar CRE configuration. In particular, FIG. 7 shows the absolute values of truncation term coefficients $c^{TCRE}(\alpha, k)$ as a function of the inner ring radius ratio $\alpha$ for truncation term order k ranging from 6 to 12. As described previously, the system may use a $5^{th}$ percentile (corresponding to the absolute value of the truncation term coefficient equal to 0.2) to determine the boundary value of a for the lowest nonzero truncation term (of order 2n+2=6), resulting in the boundary value $\alpha$=0.22. Accordingly, the optimal range of separations between the central disc and the inner concentric ring of radius $\alpha$r that keeps absolute values of the sixth order truncation term coefficients within the $5^{th}$ percentile is determined by inequality 0<$\alpha$≤0.22.

Figure 8A:
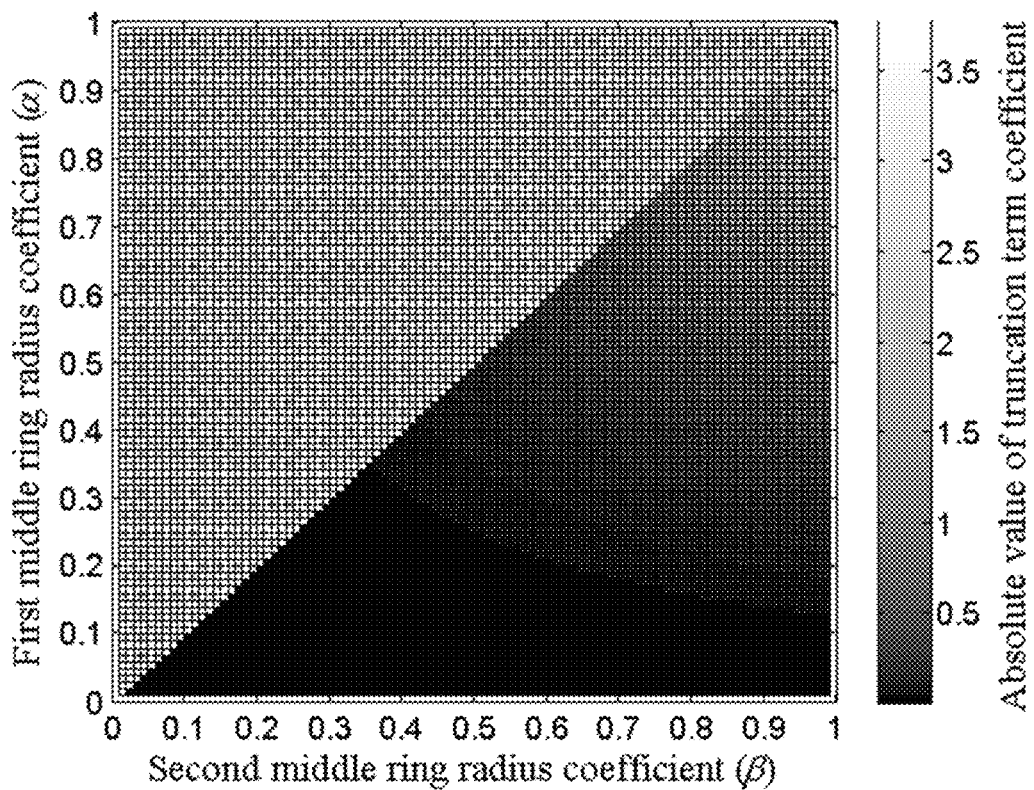
FIG. 8A illustrates the relationship between the innermost ring radius ratio α and the middle ring radius ratio β and the associated eighth-order truncation term coefficients for a quadripolar CRE configuration.

FIG. 8A illustrates the relationship between the innermost ring radius ratio $\alpha$ and the middle ring radius ratio $\beta$ and the associated eighth-order truncation term coefficients for a quadripolar CRE configuration. In particular, FIG. 8A shows absolute values of the truncation term coefficients $c^{QCRE}(\alpha, \beta, k)$ for all the combinations of the innermost radius ratio $\alpha$ and the middle ring radius ratio $\beta$ (satisfying 0<$\alpha$<$\beta$<1) for a QCRE configuration and for the lowest nonzero truncation term (i.e., of order k=2n+2=8).

Figure 8B:
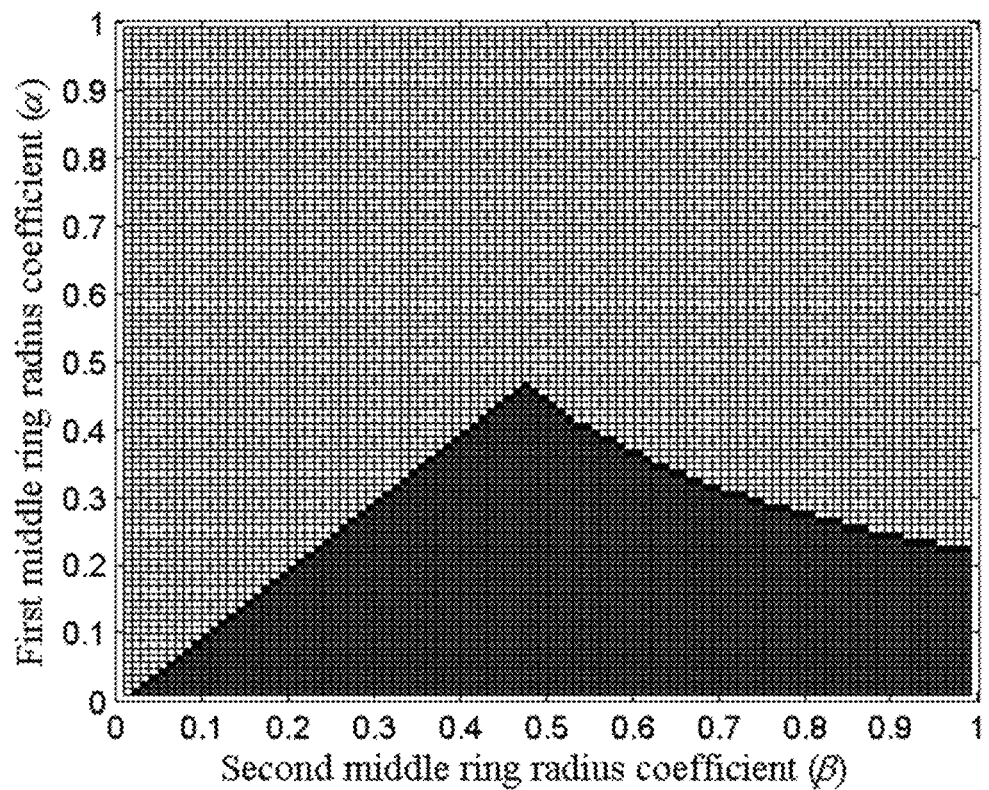
FIG. 8B illustrates absolute values of truncation term coefficients within the $5^{th}$ percentile along with the boundary separating them from the values outside of the $5^{th}$ percentile for innermost ring radius ratio α and the middle ring radius ratio β for a quadripolar CRE configuration.

FIG. 8B illustrates absolute values of truncation term coefficients within the $5^{th}$ percentile along with the boundary separating them from the values outside of the $5^{th}$ percentile for innermost ring radius ratio $\alpha$ and the middle ring radius ratio $\beta$ for a quadripolar CRE configuration. As described above, the $5^{th}$ percentile (corresponding to the absolute value of the truncation term coefficient equal to 0.19) was used to find the boundary values of $\alpha$ and $\beta$ that determine the optimal range of separations between the central disc and both the innermost and middle concentric rings, of radius $\alpha$r and $\beta$r respectively, keeping absolute values of the eighth-order truncation term coefficients within the $5^{th}$ percentile.

While the linear portion of the boundary (i.e., the left-hand side of FIG. 8B) is described by the inequality $\alpha$<$\beta$, the nonlinear portion (right-hand side) may be fitted with a curve. Based on the shape of the nonlinear portion of the boundary, a rectangular hyperbola model may be chosen. In this example, even the simplest rectangular hyperbola model $\alpha$=m/$\beta$, with m a real constant, provides a good fit to the data for m=0.21. Goodness-of-fit metric R-squared indicates that the model fit explained 99.79% of the total variation in the data.

Therefore, the optimal range of separations between the central disc and the inner and middle concentric rings with radii $\alpha$r and $\beta$r, keeping the absolute values of the eighth-order truncation term coefficient within the $5^{th}$ percentile, is determined by the inequalities 0<$\alpha$<$\beta$<1 and $\alpha$≤0.21/$\beta$ or, equivalently, $\alpha\beta$≤0.21.

Figure 9:
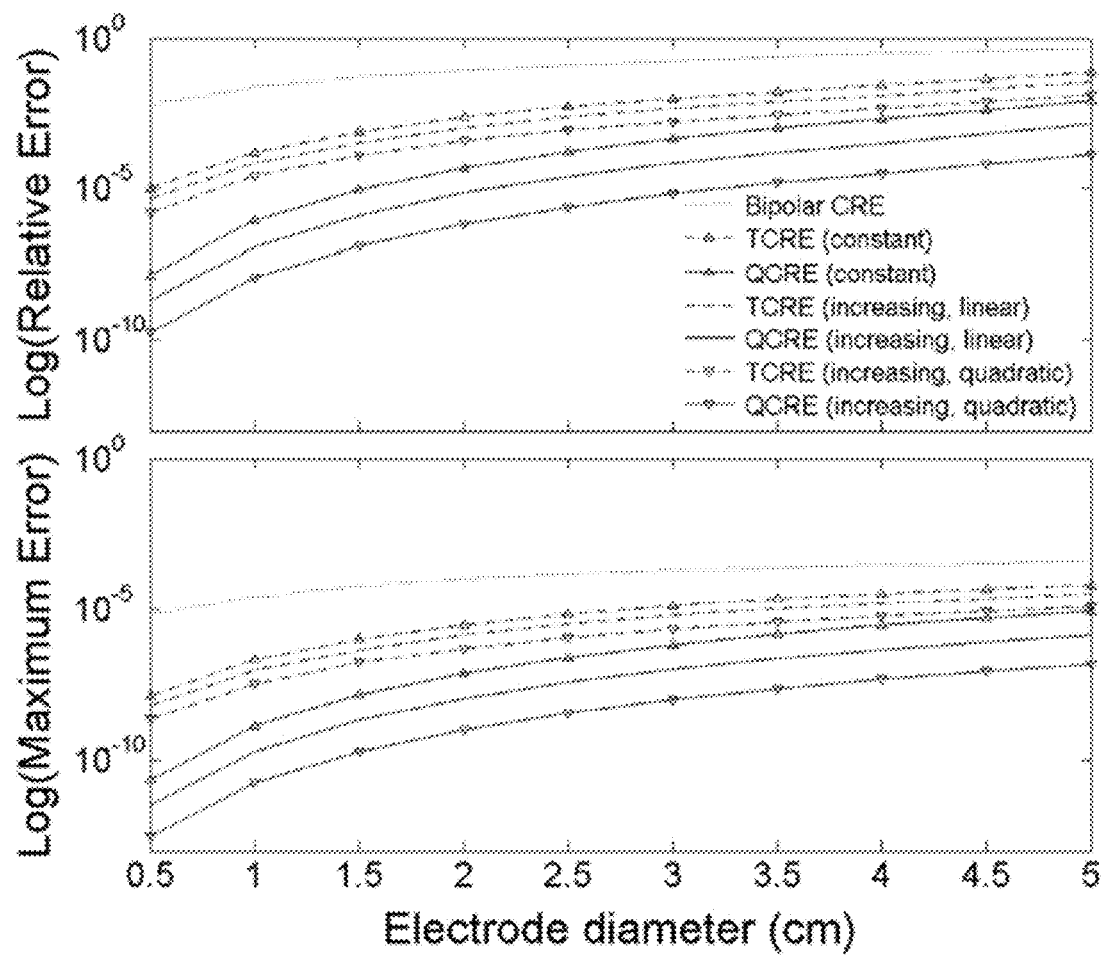
FIG. 9 illustrates relative and maximum errors for seven Laplacian estimates corresponding to bipolar CRE, tripolar CRE (TCRE), and quadripolar CRE (QCRE) configurations.

FIG. 9 illustrates relative and maximum errors for seven Laplacian estimates corresponding to bipolar CRE, TCRE, and QCRE configurations obtained via finite-element method (FEM) modeling and presented on a semi-log scale for CRE diameters ranging from 0.5 cm to 5 cm.

These FEM results suggest that TCRE and QCRE configurations with quadratically increasing inter-ring separations may improve Laplacian estimation errors over constant and linearly increasing inter-ring separations. Moreover, the improvement appears to become more significant with increasing number of rings (i.e. there is more improvement for the QCRE configuration in comparison with the TCRE one). This stems from comparison of averages (mean±standard deviation for 10 different sizes of each CRE configuration) of errors for CREs with linearly increasing inter-ring separations and quadratically increasing inter-ring separations.

VI. System

Figure 10A:
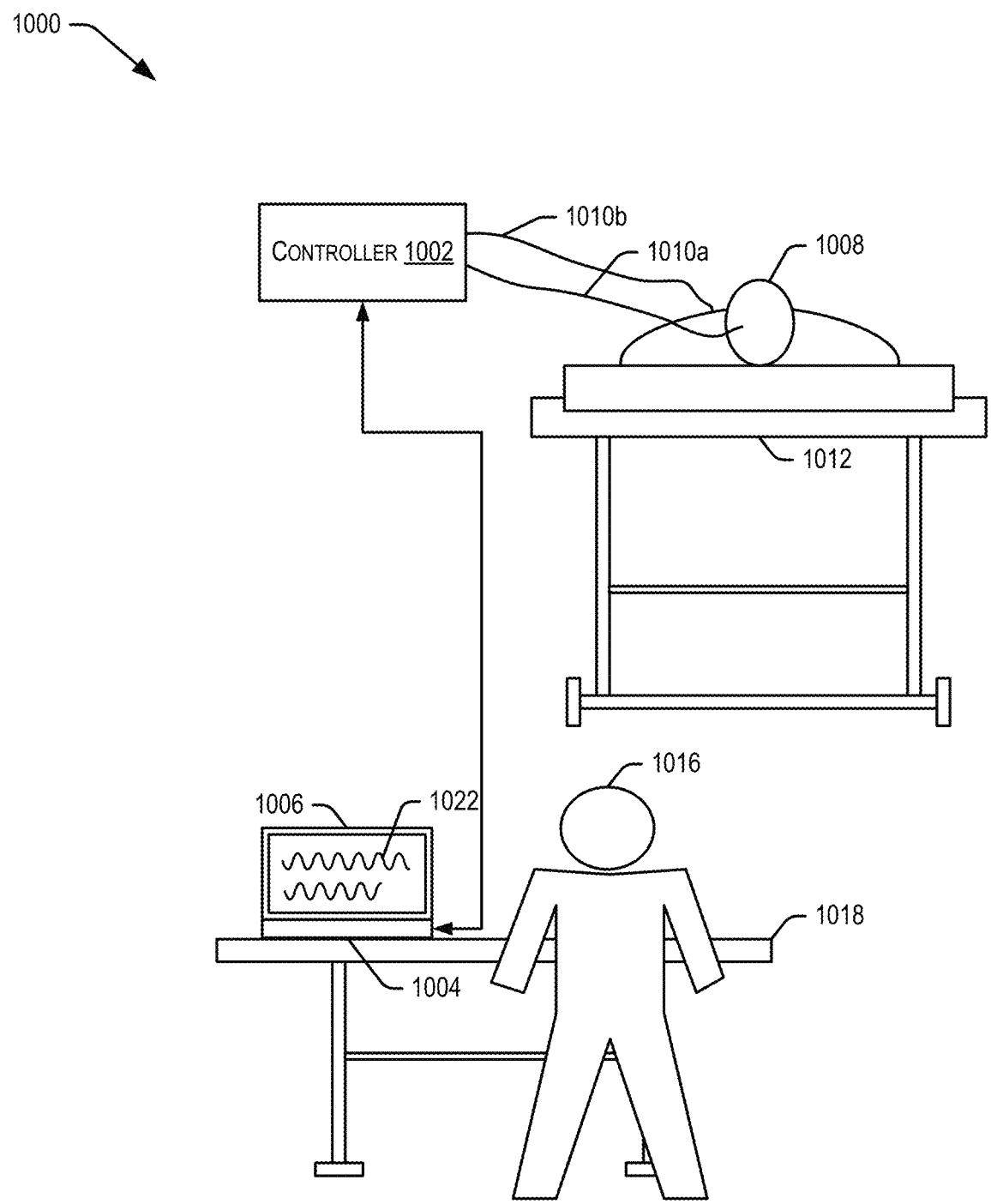
FIG. 10A illustrates an example neurophysiological monitoring system, according to at least one example.

FIG. 10A illustrates an example neurophysiological monitoring system 1000, according to at least one example. The neurophysiological monitoring system 1000 includes a monitoring system including a controller 1002 and a computing device 1004, and a display system including a display device 1006. The controller 1002 and the display device 1006 may be electronically connected to the computing device 1004 in any suitable manner (e.g., network cables, wireless networks, optical cables, power cables, input/output interfaces, etc.).

Generally, the computing device 1004, which may be any suitable computing device, is configured to manage the operation of the controller 1002 and generate and provide information for presentation at the display device 1006. The controller 1002, operating under at least partial control of the computing device 1004, may be configured to generate, deliver, detect, and/or process electrical signals with respect to a patient 1008, such as a patient undergoing EEG, brain-computer interfaces, seizure onset detection, detection of high-frequency oscillations and seizure onset zones, as well as in applications involving electroenterograms, electrocardiograms (ECG), electrohysterograms, or any other kind of electrophysiological monitoring. In particular, a CRE may measure the surface Laplacian, or the second spatial derivative, of the electrostatic potential on the patient's scalp surface. Thus, the controller 1002 may be an example of a multimodal machine for simultaneous signal generation, detection, and recording. Such signals may be referred to as neurological data or electrophysiological data. In some examples, the controller 1002 may receive commands from the computing device 1004 to send electrical signals to the patient 1008. Response signals may be detected or generated by the patient 1008 in response to electrical signals from the controller 1002. These response signals are passed by the controller 1002, which may perform some filtering and/or processing, to the computing device 1004. The computing device 1004, executing monitoring modules (e.g., dedicated hardware, firmware, or software), may be configured to receive, augment, and/or otherwise process the response signals prior to providing representations of the response signals for presentation at the display devices 1006. The modules of the computing device 1004 may allow simultaneous viewing of multiple tests. In some examples, the tests are viewed on the display device 1006.

The system may monitor and/or stimulate the patient 1008, e.g. for seizure detection and/or control or brain/computer interface, via one or more electrodes 1010a, 1010b, such as a CRE. The monitoring may occur as electrical signals are introduced at the second electrode 1010b and then detected by the first electrode 1010a. In an embodiment, a plurality of CREs may also be arranged in arrays, such as regular arrays, in order to monitor and/or map out the Laplacian of the potential at different locations on or near a patient. Note that, using coefficients and/or a formula as disclosed herein, an individual CRE or each respective CRE in an array may measure the Laplacian directly, thereby reducing the computational burden for system 1000 and/or a separate computer to compute the Laplacian. In an embodiment, such an array may be rectangular. In an embodiment, the disclosed system can also interpolate between the individual CREs in an array, in order to obtain a more detailed map of the potential and/or the Laplacian.

In some examples, the patient 1008 may be situated on an operating table 1012. The operating table 1012 may be fixed or mobile, and may include adjustability. In some examples, the operating table 1012 may include grounding connections, adapters for supporting the electrodes 1010 and/or components of the controller 1002.

In some embodiments, the display device 1006 may be positioned away from the patient 1008. For example, the display device 1006 may be supported by a table 1018. The display device 1006 may be electronically and/or physically connected to the computing device 1004. For example, the computing device 1004 may be a laptop and the display device 1006 may be a monitor of the laptop.

In some examples, the positioning of the display device 1006 may be relative to a user 1016 such as a clinically trained and certified technologist. For example, the display device 1006 may be positioned such that a display surface of the display device 1006 is viewable (e.g., within a field of view) of the user 1016.

Figure 10B:
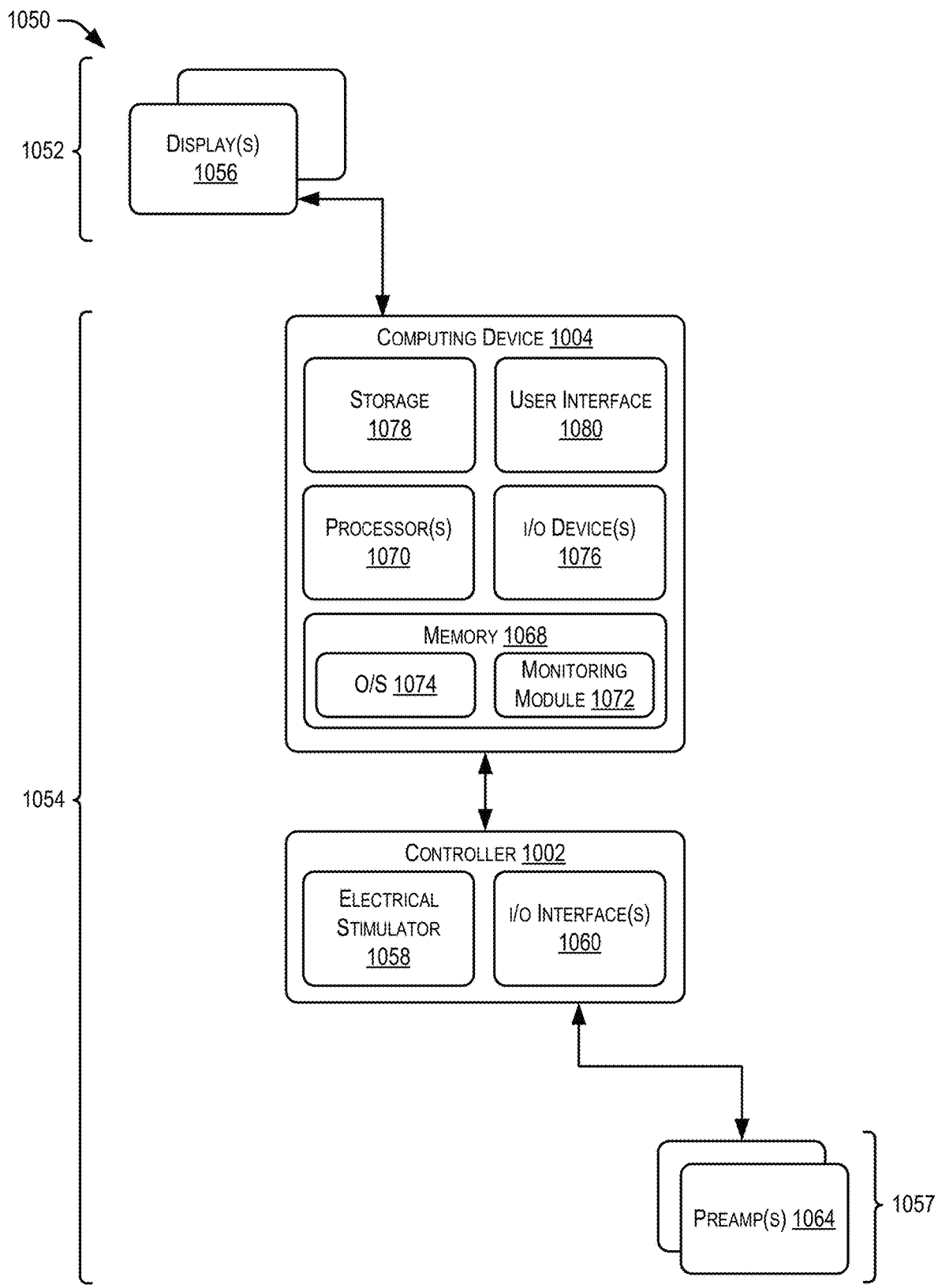
FIG. 10B illustrates components of an example neurophysiological monitoring system, according at least one example.

FIG. 10B illustrates components of an example neurophysiological monitoring system 1050, according at least one example. The neurophysiological monitoring system 1050 is an example of the neurophysiological monitoring system 1000 described herein. Thus, the neurophysiological monitoring system 1050 includes a display system 1052 and a monitoring system 1054. Like the display system described with reference to FIG. 10A, the display system 1052 includes one or more display devices such as display devices 1056. Like the display devices 1006, the display devices 1056 may be any suitable device capable of visually presenting information. Examples of such devices may include cathode ray tube (CRT) displays, light-emitting diode (LED) displays, electroluminescent displays (ELD), electronic paper, plasma display panels (PDP), liquid crystal displays (LCD), organic light-emitting diode (OLED) displays, surface-conduction electron-emitter displays (SED), field emission displays (FED), projectors (LCD, CRT, digital light processing (DLP), liquid crystal on silicon (LCoS), LED, hybrid LED, laser diode), and any other suitable device capable of displaying information.

The display devices 1056 may be positioned adjacent to the users 1016.

The monitoring system 1054 is an example of the monitoring system described with reference to FIG. 10A. To this end, the monitoring system 1054 may include the computing device 1004, the controller 1002, and one or more attachment devices 1057. The attachment devices 1057 may be connected to the controller 1002 in order to augment or otherwise enable certain functions of the controller 1002. In some examples, the attachment devices 1057 are themselves separate modules that are disposed between the controller 1002 and the patient 1008. The function of the example attachment devices 1057 will be discussed later. Though a few examples of attachment devices 1057 are illustrated, other and different attachment devices 1057 may also be connected to the controller 1002.

In various embodiments, either the controller 1002 or the computing device 1004 may store the linear combination coefficients for the potentials measured by the CRE. For example, an amplifier or preamplifier 1064 included in or associated with controller 1002 may be configured to calculate a Laplacian estimate from the potentials based on the coefficients. In some embodiments, the system 1000 (such as controller 1002 or computing device 1004) may receive and store the coefficients.

In some embodiments, the controller 1002 may include an electrical stimulator 1058 and one or more input/output interfaces 1060. The electrical stimulator 1058 may include a wide variety of triggering modes and pulse outputs to provide electrical stimulation for a patient's nervous system. In some examples, the system may instead measure, detect, and/or image a patient or a target signal, such as an EEG signal, without stimulating the patient or target.

The attachment devices 1057 also include one or more preamplifiers 1064. The preamplifiers 1064 are examples of digital preamplifier modules. In some examples, the preamplifiers 1064 provide signal detection, amplification, montage selection, A/D conversion, antialiasing filtering, and digital signal processing. The preamplifiers 1064 may route detected signals to the controller 1002 via any suitable connection. Each preamplifier 1064 may include inputs for the electrodes 1010, such as a CRE and/or the recording sites of a CRE. The preamplifiers 1064 may calculate a Laplacian estimate signal based on linear combination coefficients computed as disclosed herein.

The computing device 1004 may be in communication with the other components of the neurophysiological monitoring system 1050 via one or more network(s), wired connections, and the like. The network may include any one or a combination of many different types of networks, such as cable networks, the Internet, wireless networks, cellular networks, radio networks, and other private and/or public networks.

Turning now to the details of the computing device 1004, the computing device 1004 may include at least one memory 1068 and one or more processing units (or processor(s)) 1070. The processor(s) 1070 may be implemented as appropriate in hardware, computer-executable instructions, software, firmware, or combinations thereof. For example, the processors 1070 may include one or more general purpose computers, dedicated microprocessors, or other processing devices capable of communicating electronic information. Examples of the processors 1070 include one or more application-specific integrated circuits (ASICs), field programmable gate arrays (FPGAs), digital signal processors (DSPs) and any other suitable specific or general purpose processors.

Computer-executable instruction, software, or firmware implementations of the processor(s) 1070 may include computer-executable or machine-executable instructions written in any suitable programming language to perform the various functions described. The memory 1068 may include more than one memory and may be distributed throughout the computing device 1004. The memory 1068 may store program instructions (e.g., a monitoring module 1072) that are loadable and executable on the processor(s) 1070, as well as data generated during the execution of these programs. Depending on the configuration and type of memory including the monitoring module 1072, the memory 1068 may be volatile (such as random access memory (RAM)) and/or non-volatile (such as read-only memory (ROM), flash memory, or other memory). In an embodiment, the monitoring module 1072 may receive and/or adjust the linear combination coefficients for Laplacian estimation based on the potentials measured by the CRE. In an embodiment, monitoring module 1072 may implement the linear combination based on these coefficients. The computing device 1004 may also include additional removable storage 1078 and/or non-removable storage including, but not limited to, magnetic storage, optical disks, and/or tape storage. The disk drives and their associated computer-readable media may provide non-volatile storage of computer-readable instructions, data structures, program modules, and other data for the computing devices. In some implementations, the memory 1068 may include multiple different types of memory, such as static random access memory (SRAM), dynamic random access memory (DRAM), or ROM. The memory 1068 may also include an operating system 1074.

The memory 1068 and the additional storage 1078, both removable and non-removable, are examples of computer-readable storage media. For example, computer-readable storage media may include volatile or non-volatile, removable, or non-removable media implemented in any suitable method or technology for storage of information such as computer-readable instructions, data structures, program modules, or other data. As used herein, modules may refer to programming modules executed by computing systems (e.g., processors) that are part of the monitoring module 1072. The modules of the monitoring module 1072 may include one or more components, modules, and the like. For example, monitoring module 1072 may include modules or components that receive, adjust, and/or implement the linear combination coefficients for Laplacian estimation based on the potentials measured by the CRE. The computing device 1004 may also include input/output ("I/O") device(s) and/or ports 1076, such as for enabling connection with a keyboard, a mouse, a pen, a voice input device, a touch input device, a display, speakers, a printer, or other I/O device. The I/O device(s) 1076 may enable communication with the other systems of the neurophysiological monitoring system 1050.

The computing device 1004 may include a user interface 1080. The user interface 1080 may be utilized by an operator or other authorized user such as the user 1016 to access portions of the computing device 1004 (e.g., the monitoring module 1072). In some examples, the user interface 1080 may include a graphical user interface, web-based applications, programmatic interfaces such as application programming interfaces (APIs), or other user interface configurations.

Figure 11:
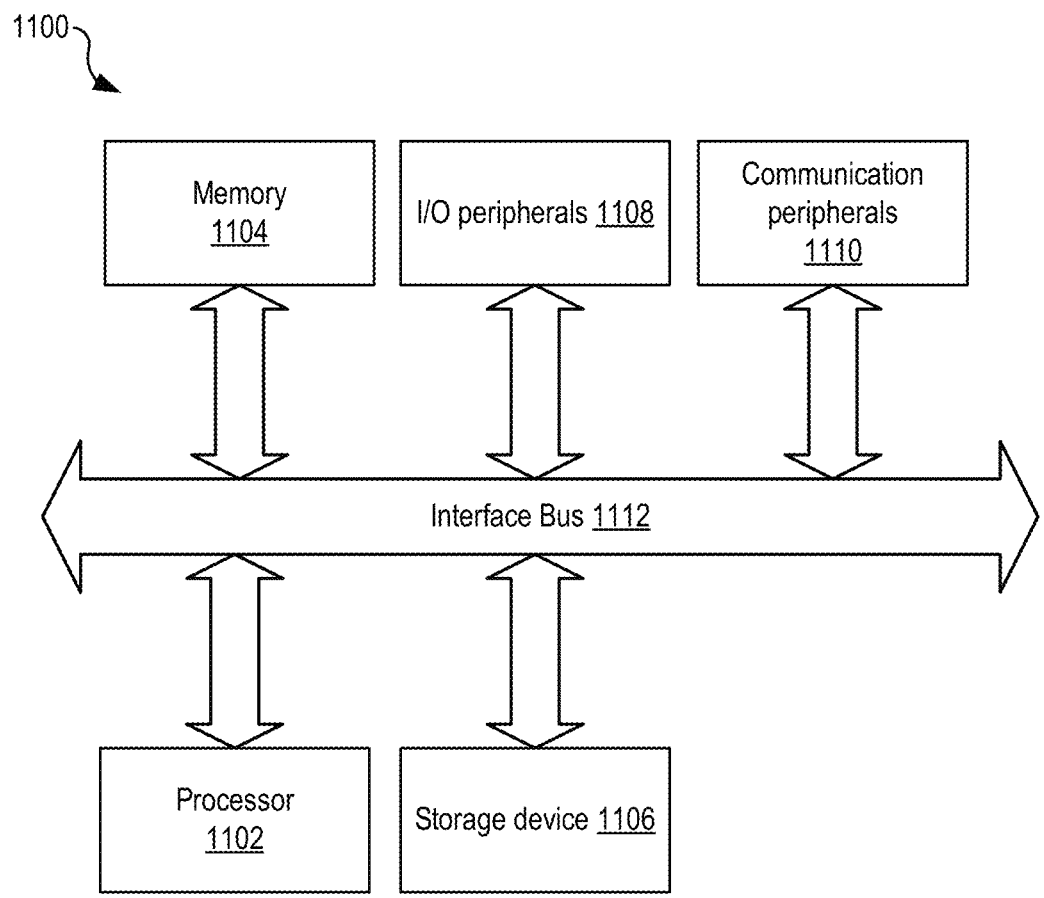
FIG. 11 illustrates examples of components of a computer system, according to at least one example.

FIG. 11 illustrates examples of components of a computer system 1100, according to at least one example. The computer system 1100 may be a single computer such as a user computing device and/or can represent a distributed computing system such as one or more server computing devices.

The computer system 1100 may include at least a processor 1102, a memory 1104, a storage device 1106, input/output peripherals (I/O) 1108, communication peripherals 1110, and an interface bus 1112. The interface bus 1112 is configured to communicate, transmit, and transfer data, controls, and commands among the various components of the computer system 1100. The memory 1104 and the storage device 1106 include computer-readable storage media, such as Radom Access Memory (RAM), Read ROM, electrically erasable programmable read-only memory (EEPROM), hard drives, CD-ROMs, optical storage devices, magnetic storage devices, electronic non-volatile computer storage, for example FLASH® memory, and other tangible storage media. Any of such computer-readable storage media can be configured to store instructions or program codes embodying aspects of the disclosure. The memory 1104 and the storage device 1106 also include computer-readable signal media. A computer-readable signal medium includes a propagated data signal with computer-readable program code embodied therein. Such a propagated signal takes any of a variety of forms including, but not limited to, electromagnetic, optical, or any combination thereof. A computer-readable signal medium includes any computer-readable medium that is not a computer-readable storage medium and that can communicate, propagate, or transport a program for use in connection with the computer system 1100.

Further, the memory 1104 includes an operating system, programs, and applications. The processor 1102 is configured to execute the stored instructions and includes, for example, a logical processing unit, a microprocessor, a digital signal processor, and other processors. The memory 1104 and/or the processor 1102 can be virtualized and can be hosted within another computing system of, for example, a cloud network or a data center. The I/O peripherals 1108 include user interfaces, such as a keyboard, screen (e.g., a touch screen), microphone, speaker, other input/output devices, and computing components, such as graphical processing units, serial ports, parallel ports, universal serial buses, and other input/output peripherals. The I/O peripherals 1108 are connected to the processor 1102 through any of the ports coupled to the interface bus 1112. The communication peripherals 1110 are configured to facilitate communication between the computer system 1100 and other computing devices over a communications network and include, for example, a network interface controller, modem, wireless and wired interface cards, antenna, and other communication peripherals.

While the present subject matter has been described in detail with respect to specific embodiments thereof, it will be appreciated that those skilled in the art, upon attaining an understanding of the foregoing may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art. Indeed, the methods and systems described herein may be embodied in a variety of other forms; furthermore, various omissions, substitutions and changes in the form of the methods and systems described herein may be made without departing from the spirit of the present disclosure. The accompanying claims and their equivalents are intended to cover such forms or modifications as would fall within the scope and spirit of the present disclosure.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provide a result conditioned on one or more inputs. Suitable computing devices include multipurpose microprocessor-based computing systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

Conditional language used herein, such as, among others, "can," "could," "might," "may," "e.g.," and the like, unless specifically stated otherwise, or otherwise understood within the context as used, is generally intended to convey that certain examples include, while other examples do not include, certain features, elements, and/or steps. Thus, such conditional language is not generally intended to imply that features, elements and/or steps are in any way required for one or more examples or that one or more examples necessarily include logic for deciding, with or without author input or prompting, whether these features, elements and/or steps are included or are to be performed in any particular example.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Similarly, the use of "based at least in part on" is meant to be open and inclusive, in that a process, step, calculation, or other action "based at least in part on" one or more recited conditions or values may, in practice, be based on additional conditions or values beyond those recited. Headings, lists, and numbering included herein are for ease of explanation only and are not meant to be limiting.

The various features and processes described above may be used independently of one another, or may be combined in various ways. All possible combinations and sub-combinations are intended to fall within the scope of the present disclosure. In addition, certain method or process blocks may be omitted in some implementations. The methods and processes described herein are also not limited to any particular sequence, and the blocks or states relating thereto can be performed in other sequences that are appropriate. For example, described blocks or states may be performed in an order other than that specifically disclosed, or multiple blocks or states may be combined in a single block or state. The example blocks or states may be performed in serial, in parallel, or in some other manner. Blocks or states may be added to or removed from the disclosed examples. Similarly, the example systems and components described herein may be configured differently than described. For example, elements may be added to, removed from, or rearranged compared to the disclosed examples.

What is claimed is:

1. A computer-implemented method for determining values for a set of radii of a plurality of rings of a concentric ring electrode (CRE), the plurality of rings comprising an inner ring and an outer ring, the method comprising:
receiving information specifying a quantity of rings in the plurality of rings;
estimating, based on canceling at least a first truncation term of a series expansion of an electrostatic potential, a dependence of a functional of the electrostatic potential on (i) a total radius of the CRE, (ii) the set of radii, and (iii) a set of potential differences, wherein a respective radius and a respective potential difference are associated with a respective ring of the plurality of rings;
determining a remaining truncation term of the series expansion as a function of the total radius and the set of radii, the remaining truncation term having a lowest order higher than twice the quantity of rings; and
minimizing in absolute value the remaining truncation term as the function of the set of radii to determine optimum values for the set of radii in terms of the total radius, wherein the determined optimum values for the set of radii indicate that:
a radius of the outer ring substantially equals the total radius of the CRE; and
an optimum radius of the inner ring is less than 23% of the total radius.

2. The computer-implemented method of claim 1, wherein the determined optimum values for the set of radii optimize a measurement accuracy by the CRE of the functional of the electrostatic potential.

3. The computer-implemented method of claim 1, wherein the optimum values are determined as a proportion of the total radius of the CRE.

4. The computer-implemented method of claim 1, wherein the plurality of rings includes at least three rings.

5. The computer-implemented method of claim 4, wherein the determined optimum values for the set of radii indicate that:
a radius of the outer ring substantially equals the total radius of the CRE; and
a product of all radii of the plurality of rings is less than 22% of the power of the total radius of the CRE equal to the quantity of the rings in the plurality of rings.

6. The computer-implemented method of claim 1, wherein the plurality of rings includes at least four rings.

7. The computer-implemented method of claim 1, wherein at least one of estimating the remaining truncation term or estimating the dependence of the functional further comprises averaging the series expansion of the electrostatic potential over areas of at least one of a central disc or the plurality of rings.

8. A method of forming a concentric ring electrode (CRE) having a plurality of rings comprising an inner ring and an outer ring, the method comprising:
receiving information specifying a quantity of rings in the plurality of rings;
estimating, based on canceling at least a first truncation term of a series expansion of an electrostatic potential, a dependence of a functional of the electrostatic potential on (i) a total radius of the CRE, (ii) a set of radii, and (iii) a set of potential differences, wherein a respective radius of the set of radii and a respective potential difference of the set of potential differences are associated with a respective ring of the plurality of rings;
determining a remaining truncation term of the series expansion as a function of the total radius and the set of radii, the remaining truncation term having an order higher than twice the quantity of rings;
minimizing in absolute value the remaining truncation term as the function of the set of radii to determine optimum values for the set of radii in terms of the total radius, wherein the determined optimum values for the set of radii indicate that:
a radius of the outer ring substantially equals the total radius of the CRE; and
an optimum radius of the inner ring is less than 23% of the total radius; and
forming the inner ring and the outer ring to have radii based on the total radius and the determined optimum values.

9. The method of claim 8, further comprising:
providing a non-conductive substrate;
depositing and/or forming a plurality of rings on the non-conductive substrate; and
electrically coupling one or more rings of the plurality of rings with one or more terminals connected to an interface.

10. The method of claim 9, wherein the non-conductive substrate is flexible and biocompatible, and wherein depositing and/or forming the plurality of rings further comprises printing the plurality of rings on the non-conductive substrate.

11. The method of claim 8, wherein the series expansion is a Taylor expansion.

12. The method of claim 8, wherein estimating the dependence of the functional is further based on canceling multiple truncation terms, and wherein an order of the canceled first truncation term equals twice the quantity of rings.

13. The method of claim 8, wherein the functional comprises a Laplacian of the electrostatic potential.

14. A non-transitory computer-readable storage medium storing instructions, that upon execution on a computer system, cause the computer system to perform a method for determining values for a set of radii of a plurality of rings of a concentric ring electrode (CRE), the plurality of rings comprising an inner ring and an outer ring, the method comprising:
receiving information specifying a quantity of rings in the plurality of rings;
estimating, based on canceling at least a first truncation term of a series expansion of an electrostatic potential, a dependence of a functional of the electrostatic potential on (i) a total radius of the CRE, (ii) the set of radii, and (iii) a set of potential differences, wherein a respective radius and a respective potential difference are associated with a respective ring of the plurality of rings;
determining a remaining truncation term of the series expansion as a function of the total radius and the set of radii, the remaining truncation term having an order higher than twice the quantity of rings; and
minimizing in absolute value the remaining truncation term as the function of the set of radii to determine optimum values for the set of radii in terms of the total radius, wherein minimizing in absolute value the remaining truncation term comprises minimizing, within a percentile value, an absolute value of the remaining truncation term having the lowest order, based on the function of the set of radii.

15. The non-transitory computer-readable storage medium of claim 14, wherein:
the plurality of rings includes at least four rings; and
forming the inner ring and the outer ring further comprises forming the four rings to have radii based on the total radius and the determined optimum values.

16. The non-transitory computer-readable storage medium of claim 14, wherein an order of the first truncation term equals twice the quantity of rings.

17. The non-transitory computer-readable storage medium of claim 14, wherein:
a number of radii in the set of radii equals the quantity of rings; and
a number of potential differences in the set of potential differences equals the quantity of rings.

18. The non-transitory computer-readable storage medium of claim 14, wherein the determined optimum values for the set of radii specify optimum values for inter-ring separations of the plurality of rings.

19. A computer-implemented method for determining values for a set of radii of a plurality of rings of a concentric ring electrode (CRE), the plurality of rings comprising at least three rings including an inner ring and an outer ring, the method comprising:
- receiving information specifying a quantity of rings in the plurality of rings;
- estimating, based on canceling at least a first truncation term of a series expansion of an electrostatic potential, a dependence of a functional of the electrostatic potential on (i) a total radius of the CRE, (ii) the set of radii, and (iii) a set of potential differences, wherein a respective radius and a respective potential difference are associated with a respective ring of the plurality of rings;
- determining a remaining truncation term of the series expansion as a function of the total radius and the set of radii, the remaining truncation term having a lowest order higher than twice the quantity of rings; and
- minimizing in absolute value the remaining truncation term as the function of the set of radii to determine optimum values for the set of radii in terms of the total radius, wherein the determined optimum values for the set of radii indicate that:
  - a radius of the outer ring substantially equals the total radius of the CRE; and
  - a product of all radii of the plurality of rings is less than 22% of the power of the total radius of the CRE equal to the quantity of the rings in the plurality of rings.

20. The computer-implemented method of claim 19, wherein the determined optimum values for the set of radii optimize a measurement accuracy by the CRE of the functional of the electrostatic potential.

21. The computer-implemented method of claim 19, wherein the optimum values are determined as a proportion of the total radius of the CRE.

22. The computer-implemented method of claim 19, wherein the plurality of rings includes at least three rings.

23. The computer-implemented method of claim 19, wherein the plurality of rings includes at least four rings.

24. The computer-implemented method of claim 19, wherein at least one of estimating the remaining truncation term or estimating the dependence of the functional further comprises averaging the series expansion of the electrostatic potential over areas of at least one of a central disc or the plurality of rings.

25. A non-transitory computer-readable storage medium storing instructions, that upon execution on a computer system, cause the computer system to perform a method for determining values for a set of radii of a plurality of rings of a concentric ring electrode (CRE), the plurality of rings comprising an inner ring and an outer ring, the method comprising:
- receiving information specifying a quantity of rings in the plurality of rings;
- estimating, based on canceling at least a first truncation term of a series expansion of an electrostatic potential, a dependence of a functional of the electrostatic potential on (i) a total radius of the CRE, (ii) the set of radii, and (iii) a set of potential differences, wherein a respective radius and a respective potential difference are associated with a respective ring of the plurality of rings;
- determining a remaining truncation term of the series expansion as a function of the total radius and the set of radii, the remaining truncation term having an order higher than twice the quantity of rings; and
- minimizing in absolute value the remaining truncation term as the function of the set of radii to determine optimum values for the set of radii in terms of the total radius, wherein the determined optimum values for the set of radii specify optimum values for inter-ring separations of the plurality of rings.

26. The non-transitory computer-readable storage medium of claim 25, wherein:
- the plurality of rings includes at least four rings; and
- forming the inner ring and the outer ring further comprises forming the four rings to have radii based on the total radius and the determined optimum values.

27. The non-transitory computer-readable storage medium of claim 25, wherein an order of the first truncation term equals twice the quantity of rings.

28. The non-transitory computer-readable storage medium of claim 25, wherein minimizing in absolute value the remaining truncation term comprises minimizing, within a percentile value, an absolute value of the remaining truncation term having the lowest order, based on the function of the set of radii.

29. The non-transitory computer-readable storage medium of claim 25, wherein:
- a number of radii in the set of radii equals the quantity of rings; and
- a number of potential differences in the set of potential differences equals the quantity of rings.

30. A method of forming a concentric ring electrode (CRE) having a plurality of rings comprising an inner ring and an outer ring, the method comprising:
- receiving information specifying a quantity of rings in the plurality of rings;
- estimating, based on canceling at least a first truncation term of a series expansion of an electrostatic potential, a dependence of a functional of the electrostatic potential on (i) a total radius of the CRE, (ii) a set of radii, and (iii) a set of potential differences, wherein a respective radius of the set of radii and a respective potential difference of the set of potential differences are associated with a respective ring of the plurality of rings;
- determining a remaining truncation term of the series expansion as a function of the total radius and the set of radii, the remaining truncation term having an order higher than twice the quantity of rings;
- minimizing in absolute value the remaining truncation term as the function of the set of radii to determine optimum values for the set of radii in terms of the total radius by at least minimizing, within a percentile value, an absolute value of the remaining truncation term having the lowest order, based on the function of the set of radii; and
- forming the inner ring and the outer ring to have radii based on the total radius and the determined optimum values.

31. The method of claim 30, further comprising:
providing a non-conductive substrate;
depositing and/or forming a plurality of rings on the non-conductive substrate; and
electrically coupling one or more rings of the plurality of rings with one or more terminals connected to an interface.

32. The method of claim 31, wherein the non-conductive substrate is flexible and biocompatible, and wherein depositing and/or forming the plurality of rings further comprises printing the plurality of rings on the non-conductive substrate.

33. The method of claim 30, wherein the series expansion is a Taylor expansion.

34. The method of claim 30, wherein estimating the dependence of the functional is further based on canceling multiple truncation terms, and wherein an order of the canceled first truncation term equals twice the quantity of rings.

35. The method of claim 30, wherein the functional comprises a Laplacian of the electrostatic potential.

* * * * *